(12) United States Patent
Madsen et al.

(10) Patent No.: US 8,426,668 B2
(45) Date of Patent: Apr. 23, 2013

(54) DRESSING PRODUCT

(75) Inventors: Lotte Madsen, Holte (DK);
Anne-Marie Søbye Rapp, Vedbaek (DK); Grazyna Hansen, Frederiksberg (DK); Bjoern Christiansen, Hilleroed (DK); Jan Marcussen, Taastrup (DK); Troels Schoenfeldt, Espergaerde (DK); Morten Thomsen, Frederiksberg (DK)

(73) Assignee: Colopast A/S, Humlebaek (DK)

( * ) Notice: Subject to any disclaimer, the term of this patent is extended or adjusted under 35 U.S.C. 154(b) by 0 days.

(21) Appl. No.: 12/946,976

(22) Filed: Nov. 16, 2010

(65) Prior Publication Data
US 2011/0190678 A1 Aug. 4, 2011

Related U.S. Application Data

(63) Continuation of application No. 10/581,048, filed on Apr. 5, 2007, now Pat. No. 7,880,051.

(30) Foreign Application Priority Data

Nov. 28, 2003 (DK) .................................. 2003 01763

(51) Int. Cl.
*A61F 13/00* (2006.01)
(52) U.S. Cl.
USPC .................... 602/58; 602/41; 602/52; 602/57
(58) Field of Classification Search ............... 602/41–43, 602/52, 57–59; 206/440–441; D24/189
See application file for complete search history.

(56) References Cited

U.S. PATENT DOCUMENTS

| 4,753,232 | A | 6/1988 | Ward |
| 5,628,724 | A | 5/1997 | Holmes |
| 6,303,700 | B1 * | 10/2001 | Chen .......................... 525/326.9 |
| 6,923,320 | B2 * | 8/2005 | Grossman ..................... 206/440 |

FOREIGN PATENT DOCUMENTS

| JP | 3039028 U1 | 4/1991 |
| JP | 6000201 A2 | 1/1994 |
| JP | 6063071 A2 | 3/1994 |
| WO | 9619394 A1 | 6/1996 |

OTHER PUBLICATIONS

Non-final office action dated Apr. 22, 2011 in corresponding U.S. Appl. No. 12/946,989.
Office Action mailed on Nov. 23, 2011 in U.S. Appl. No. 12/946,989.

* cited by examiner

*Primary Examiner* — Kim M Lewis
(74) *Attorney, Agent, or Firm* — Coloplast Corp., Coloplast A/S; Daniel G. Chapik; Nicholas R. Baumann

(57) ABSTRACT

A dressing product includes a cover sheet, a carrier system, and a dressing sheet. The carrier system includes a periphery that is attached to the cover sheet and a lower portion that extends from the periphery to a protruding portion. The protruding portion of the carrier system is spaced apart from the cover sheet by the lower portion of the carrier system to define a cavity between the cover sheet and the carrier system. The dressing sheet includes a backing layer and an adhesive attached to the backing layer. The dressing sheet is disposed in the cavity and is contained between sidewalls that are defined by the lower portion of the carrier system.

9 Claims, 22 Drawing Sheets

DRESSING PRODUCT

CROSS REFERENCE TO RELATED APPLICATIONS

The present application is a continuation of Ser. No. 10/581,048 filed on 5 Apr. 2007 now U.S. Pat. No. 7,880,051, which is herein incorporated by reference in its entirety.

BACKGROUND OF THE INVENTION

1. Field of the Invention

The present invention generally relates to dressings for application to e.g. a skin portion of a human, in particular to the field of thin film dressings provided in the form of backings coated on one side with an adhesive. More specifically, the invention concerns carrier systems for such dressings.

2. Description of the Related Art

Various thin flexible film adhesive coated dressings, such as wound dressings and surgical drapes and delivery systems therefore, are known. The dressings can be applied to an application site, such as a skin portion of a living being, by removing a releasable protective liner from the adhesive coating and adhering the dressing to the application site. The adhesive is usually coated onto a surface of a polymeric film.

Prior art document EP 308 122 A2 discloses an adhesive coated thin film dressing in combination with an applicator therefore, wherein the applicator comprises a pair of superposed laminar members hinged at one end, the lower member being adapted to be grasped at the end remote from the hinge and the upper member being adapted to support the dressing. The upper member is in releasable contact with a major portion of the adhesive surface therefore. A protector is provided which is in releasable contact with the remaining portion of the adhesive surface and which extends beyond the hinged end of the upper member.

WO 00/41670 discloses a Herpes Labialis plaster formed of a so-called sticking part, a sterile cloth of gauze and an elastic part, which is said to be, twisted about 90 degrees from its middle along its width.

Further delivery systems are known from U.S. Pat. No. 6,169,224 B1, U.S. Pat. No. 6,264,976 B1 and U.S. Pat. No. 5,738,642.

SUMMARY OF THE INVENTION

It is an object of preferred embodiments of the present invention to provide a dressing product with a carrier system that allows for precise and convenient application of a dressing sheet, in particular, but not exclusively, a thin film dressing sheet, i.e. to provide a carrier system which does not result in wrinkling of the dressing sheet during application thereof and which is easy to handle, e.g., during application to a facial site. It is a further object of preferred embodiments of the invention to provide a dressing product with a carrier system, which allows for easy and precise application of dressing sheets having a relatively small surface area.

Accordingly, in a first aspect the invention provides a dressing product comprising:
  a dressing sheet, one first surface of which is provided with an adhesive, whereby said first surface defines an adhering surface for attaching the dressing sheet to an anatomical surface of a living being;
  a carrier system defining a gripping section for handling of the carrier system by human fingers, the carrier system providing a support for the dressing sheet and at least a part of the carrier system is attached to the dressing sheet by means of said adhesive;
  the dressing sheet being releasably connected to or contained in the carrier system, so that the carrier system can be separated from the dressing sheet during application thereof, wherein the carrier system comprises a supporting section and a protective sheet, said supporting section and protective sheet being adjoined along a curved or linear line, wherein the adhering surface of the dressing sheet defines an overlapping region in which the sheet adheres to the supporting section, and a non-overlapping region in which the sheet does not adhere to the supporting section.

Several dressing sheets may be supported by the carrier system. For example a plurality of dressing sheets may be attached to the carrier system in an array or in any other predetermined pattern, for example in a circular fashion along a periphery of a generally circular or oval carrier system.

In the present context, the term dressing sheet should be interpreted in a broad sense, i.e. to include not only thin film dressings, but also any other kind of dressings, including other types of film dressings, dressing with absorbents, blister healing dressings, callus relief dressings, bunion relief dressings, dressings for cuts or grazes, surgical drapes etc.

Once an initial portion of the adhesive is attached to the application site, e.g. on the skin of a human, the adhesive force provided between that portion of the adhesive and the skin is preferably larger than the force needed for separating the carrier system from the dressing sheet. Accordingly, the dressing sheet may be separated from the remaining portion of the dressing sheet while the dressing sheet is gradually applied to the application site. This may be achieved by selecting an adhesive with appropriate adhesive properties and/or by selecting an appropriate surface structure of the relevant part of the carrier system. For example, in embodiments in which a part of the carrier system is directly attached to the dressing sheet by means of that adhesive, which is also used for attaching the dressing sheet to the skin, the surface structure of that part of the carrier system may be such that a smaller force is needed for releasing the dressing sheet from the carrier system than the force needed for separating the adhesive surface of the dressing sheet from the skin.

The supporting section or the protective sheet may be provided with a slit in the area not covered by the dressing sheet. The slit is enclosed by the supporting section and does thus not reach the edge of the section. Preferably, the slit is substantially parallel to the adjoining line of the supporting section and the protective sheet. In one embodiment of the invention the slit is curved, preferably to form a line being coaxial to the dressing sheet. In another embodiment of the invention the slit is in the form of connected rectilinear lines. The slits provide flexibility to the carrier system during application. When the dressing sheet is applied the protective sheet is removed by pulling away from the supporting sheet. When the sheet is pulled, the sheet will flex at the point of the slit, thus easing the removal from the adhesive. Then the unprotected adhesive part is applied to the desired application site, e.g. the skin, and the supporting section is pulled off, also flexing at the slit, providing a rolling movement of the part of the supporting section attached to the dressing sheet. The presence of the slit(s) renders it possible to release and apply the dressing sheet without twisting the dressing, which otherwise may give rise to wrinkles and tensions.

The carrier system preferably provides a relatively rigid or stiff support for the dressing sheet, so that wrinkling or crumpling of the dressing sheet can be prevented. The carrier system may thus, in addition to the gripping section, define a sheet supporting section to which the dressing sheet adheres. It may be foreseen that only a portion of a peripheral section of the adhering surface of the dressing sheet adheres to the sheet supporting section, in which case there is defined an overlapping region in which the sheet adheres to the supporting section, and a non-overlapping region in which the sheet does not adhere to the supporting section. The overlapping region is preferably large enough to ensure non-wrinkling or non-crumpling of the dressing sheet. In other words, the overlapping region should ensure that the dressing sheet is maintained in a distended manner by the sheet supporting section. The sheet supporting section may for example be O- or U-shaped.

A protective sheet may be provided for protecting the adhering surface of the dressing sheet prior to application thereof. The protective sheet may adhere to the adhering surface by means of that adhesive, which is also used for adhering the dressing sheet to the skin. In addition to this, or as an alternative, a separate, second adhesive may be provided for securing the protective member in relation to the carrier system and the dressing sheet. In case the carrier system defines a supporting section for supporting a peripheral portion of the dressing sheet, the protective sheet may adhere to the non-overlapping region, so that the non-overlapping region is exposed when the protective sheet is removed. Thereby, the carrier system can be separated from the sheet when the non-overlapping region adheres to the application site, so that the entire adhering surface can ultimately be adhered to the application site.

It has been found that application of a substance, such as pharmaceutical product, e.g. in the form of an ointment or cream, or any other substance, such as a moistening cream, a gel or a liquid in the form of a spray, to an anatomical surface, such as a skin portion of a human being, jeopardizes the adhering effects of a dressing subsequently applied to that surface. Therefore, the present inventors have proposed to apply the substance to a surface of a dressing, which in turn is applied to the application site. This new insight has resulted in a surprising and significant improvement. However, even this improved solution may have negative effects on the adhering properties of the dressing. Thus, a dressing may separate from an application site, such as a skin portion of a human being, relatively soon after its application, which is not only inconvenient to the patient wearing the dressing but which also increases costs. Accordingly, one aspect of the present invention is concerned with reducing or eliminating such negative effects. In order to solve this problem and in order to facilitate application of a pharmaceutical product to the adhering surface, the protective sheet may define at least one opening, through which a portion of the adhering surface of the dressing sheet, such as a portion of the non-overlapping region of the adhering surface, is accessible while the dressing sheet is still connected to the carrier system. The pharmaceutical substance, such as an ointment or cream, gel, liquid spray or the like may thus be applied to a confined area of the adhering surface prior to application of the dressing sheet to the application site. This has, surprisingly, shown to efficiently solve the problem of reduced adhering properties when a substance is applied to the adhering surface, as it may be ensured that substance is not applied to the entire adhering surface. For example, the protective sheet, or a plurality of protective sheets, may cover at least parts of the peripheral portions of the adhering surface, so as to ensure that no substance is applied to those parts of the peripheral portions, which in turn are ensured to provide a firm adhering effect along at least a portion of the periphery of the dressing sheet. In other words, the opening may be provided in the protective sheet such that it does not extend to the bounds of the dressing sheet, whereby application of the pharmaceutical product to a peripheral portion of the adhering surface of the dressing sheet may be efficiently prevented. Most preferably, the opening is provided centrally within the protective sheet. The opening may be provided as a cut-out section in one or more protective sheets attached to the adhering surface, or it may be provided between boundary edges of separate protective sheets. The opening may optionally be covered by a closing member, which is separately releasable from the dressing sheet or the carrier system in such a way that the protective sheet maintains attached to the dressing patch when the closing member is removed.

The provision of the opening in the protective sheet or sheets (or between protective sheets) is further advantageous for the following reasons. In case a substance, such as a pharmaceutical substance, has a relatively short disintegration time, i.e. an integration time which is shorter than the durability of other parts or portions of the dressing product, it may be inexpedient or even impossible to pre-coat the dressing product with the substance prior to delivery thereof to the end-user or to incorporate the substance in the adhesive. Therefore, such a substance can advantageously be provided in a separate container, such as a tube, in which it does not disintegrate as fast as when contained in the dressing sheet itself. Thanks to the opening in the protective sheet, the substance to be applied to the dressing product may be easily, but yet accurately, applied by an operator which in many instances is the patient himself/herself.

The amount of substance ultimately applied to the dressing patch and hence to the application site may be dependent from the thickness of the protective sheet and from the area of the opening (or the accumulated areas of a plurality of openings). Accordingly, the dressing product of the invention may be manufactured with various protective sheet thicknesses, so that the product can be tailored to a specific use, e.g. to a specific dosage of a specific medicament. The dressing product of the invention may also be provided in a kit with a plurality of such dressing products, the respective protective sheets of which have different thicknesses or opening areas, so that a patient may dose a substance, for example a medicament, by selecting a specific dressing product with a certain protective sheet thickness or opening area providing the desired dosage of the medicament.

An alternative way of controlling the amount of substance applied to the surface of the dressing is to provide one or more cavities in the dressing itself for accommodating the substance. The cavity or cavities may be in the form of a dome shaped portion or an indentation.

It has further been found that the durability of a dressing product which contains or is coated with a substance, such as a pharmaceutical substance, e.g. in the form of an ointment, cream, gel, liquid spray or the like, may have a very limited durability. This is particularly the case if the substance has a relatively short disintegration time, i.e. an integration time, which is shorter than the durability of other parts or portions of the dressing product. Thus, the durability of the entire dressing product is negatively affected by the limited durability of the substance contained in or coated onto the dressing.

Therefore, it is an object of preferred embodiments of the present invention to provide a dressing product, the durability of which is longer than the durability of at least some of the substances applicable to a surface thereof.

It is a further object of preferred embodiments of the present invention to provide a dressing product, which eliminates or at least reduces the aforementioned negative effects on adhesive abilities.

Accordingly, the invention provides a dressing product comprising: a dressing patch, one first surface of which is at least partially provided with an adhesive, whereby said first surface defines an adhering surface for attaching the dressing patch to an anatomical surface of a living being; at least one protective sheet adhering to the adhering surface of the dressing patch, wherein the at least one protective sheet defines at least one opening, through which a portion of the first surface of the dressing patch is accessible while the at least one protective sheet is connected to the dressing.

It will be appreciated that a substance, such as a pharmaceutical substance, which may be in the form of an ointment or cream, gel, liquid spray or the like may thus be applied to a confined area of the adhering surface prior to application of the dressing patch to the application site, i.e. to that area which is accessible through the at least one opening provided in or by the one or more protective sheets. This has, surprisingly, shown to efficiently solve the problem of reduced adhering properties when a substance is applied to the adhering surface, as it may be ensured that substance is not applied to the entire adhering surface. For example, the protective sheet, or a plurality of protective sheets, may cover at least parts of the peripheral portions of the surface of the dressing, so as to ensure that no substance is applied to those parts.

The protective sheet may define a folding line and two sections on either side of the folding line, with the first section adhering to the adhering surface the sheet, and the second section overlapping the first section. Accordingly, the second section may serve as a further protective sheet. For example, the cut-out section may be provided in the first section of the protective sheet, whereby the second section may protect that portion of the adhering surface of the dressing sheet which is accessible through the cut-out section. The folding line preferably defines a hinge around which the second section may be flipped to lay open the cut-out section for application of a pharmaceutical product to the adhering surface through the cut-out section.

In certain embodiments of the invention, the gripping section extends away from the dressing sheet in a direction substantially parallel to the plane defined by the dressing sheet, the gripping section having a bending stiffness, which is sufficient to control application of the dressing sheet. Accordingly, such embodiments result in a flat product, which may be conveniently and compactly packed and stored. Preferably, the dimensions and bending stiffness of the carrier system or at least of its gripping section allow the carrier system sheet to flex away from the anatomical surface of the living being in order to provide an enhanced application pressure at the application site on the one hand and in order to provide space for the fingers of the operator applying the dressing sheet on the other hand.

With the aim of ensuring a surface area of the gripping section, which is sufficient for it to be safely handled by human fingers, the gripping section may be arranged to extend beyond the bounds of the dressing sheet. Preferably, that length of the gripping section which is beyond the bounds of the dressing sheet, L, is at least equal to the largest cross-sectional dimension of the dressing sheet, D, when seen in a plane view, $L \geqq D$, such as $L \geqq 1.25*D$, such as $L \geqq 1.5*D$, such as $L \geqq 2*D$, such as $L \geqq 4*D$, such as $L \geqq 5*D$, such as $L \geqq 10*D$. For example, a dressing sheet with a diameter of 4 mm may have a gripping section with a length of, e.g., 3-5 cm. The plane view, in which the ratio between L and D meets these restrictions, may be parallel to the plane of the dressing sheet, i.e. a top view, or transverse, preferably perpendicular, to the plane of the dressing sheet. It will be appreciated that the gripping section may thus, for example, define an upright handgrip or, alternatively, a planar sheet member coextending with the plane of the dressing sheet. Very long gripping sections, for example of a length of 5-20 cm or even more may be useful in respect of dressing sheets to be applied to a patient's foot, e.g. to a wart at the sole of the foot, or at other locations remote from the operator's or patient's hands, even in case the order of magnitude of the cross-sectional dimension of the dressing sheet is 1 cm.

In some embodiments, in particular those wherein the gripping section extends substantially in the plane of the dressing sheet, the cross-sectional surface area of the gripping section, A, may be at least equal to the cross-sectional surface area of the dressing sheet, a, $A \geqq a$, such as such as $A \geqq 1.25*a$, such as $A \geqq 1.5*a$, such as $A \geqq 2*a$. Embodiments, in which the aforementioned ratios between lengths and areas, respectively, of the gripping section and the dressing sheet apply, are specifically useful when the surface area of the dressing sheet is relatively small, i.e. less than 5 cm$^2$, such as at most 4 cm$^2$, such as at most 2 cm$^2$, such as in the range of 1-2 cm$^2$ or smaller, such as 0.08-1 cm$^2$, such as 0.1-0.8 cm$^2$, such as 0.12-5 cm$^2$ rendering handling of the dressing sheet by an equally small carrier system difficult, when handling is to be carried out by human fingers. However, also larger dressings are within the scope of the present invention, including dressings with a surface area of the dressing sheet of e.g. be 5-25 cm$^2$, such as 10-20 cm$^2$.

In the carrier systems disclosed herein, the foil or sheet which is ultimately used for applying the dressing sheet to the application site may adhere to or overlap the entire adhering surface of the dressing sheet, or only a fraction thereof. Embodiments are provided wherein only a minor portion of the surface area of the foil or sheet used for application adheres to or overlaps the adhering surface. Such embodiments may be advantageous, as a relatively large portion of the adhering surface of the dressing sheet may, prior to application thereof, be exposed for application of a pharmaceutical substance and/or for secure application, as a relatively large portion of the adhering surface may be brought into contact with the application site already at the beginning of the application process, so as to prevent undesired slippage of the dressing sheet relative to the application site. It is preferred that the foil or sheet for applying the dressing sheet, irrespective of the amount of overlap with the adhering surface, is capable of maintaining the dressing sheet in a stretched or distended manner, at least until a sufficient amount of the dressing sheet, during application thereof, adheres to the application site for preventing wrinkling or crumpling of the dressing sheet.

Preferably, in order to avoid wrinkling or crumpling of the dressing sheet, the carrier system comprises a supporting sheet having a bending stiffness which, when attached to the dressing sheet, is greater than the bending stiffness of the dressing sheet without the supporting sheet being attached thereto, and without any paper web attached to the dressing sheet. In most embodiments, the supporting sheet has a bending stiffness greater than the bending stiffness of the dressing sheet. The supporting sheet may be made from paper or cardboard material or from a metal, such aluminium or from a plastics material, such as polyester, such as polyethyleneterephthalate (PETP), which may optionally be coated with one or more coatings for providing desired properties, such as releasability (i.e. adhering properties) for achieving the desired releasability effects, cf. the above discussion. The adhering properties (or releasabiilty) of the supporting sheet may thus vary in dependence of the choice of material for the coating. Suitable material groups may e.g. comprise silicone, metals, and Teflon™. It has been found that silicone materials are generally well suited for the coating, as various available silicone materials provide a useful variety of adhering properties. Once silicone materials have been identified as a suitable group of materials for the coating of the supporting surface of the carrier system, it is a matter of routine experimentation to identify that specific material, which is best suited for a particular embodiment or purpose.

Handling of the carrier system may, for certain uses, be facilitated if the bending stiffness, density and dimensions of the supporting sheet are such that essentially no deflection is caused to the supporting sheet by its own weight when the supporting sheet is supported at one end, or held by a finger at one end. This is in particular useful in embodiments in which the carrier system and thus the supporting sheet extend essentially in the plane of the dressing sheet. In respect of embodiments in which the supporting sheet is separated from the dressing sheet prior to application thereof, it is, however, of little importance for the handling during application whether or not the supporting sheet deflects under its own weight, though in terms of easy handling prior to application, it may also be desirable that it does not.

In addition to the supporting sheet, there may further be provided a flexible foil member for facilitating application of the dressing sheet. The foil member may be connected or attached to the second surface of dressing sheet, i.e. the backing layer, or to the adhering surface, for example directly to the adhesive. The foil may, e.g., be made from polyester, such as from PETP, or from paper or cardboard material, preferably coated with e.g. silicone, metal, such as aluminium, or Teflon™.

The protective sheet may comprise two or more sheet parts, wherein the at least one opening may be provided in one or more of the protective sheet parts or between boundaries thereof.

The provision of the opening in the protective sheet or sheets (or between protective sheets) is further advantageous, as it allows for separate storage of a substance, such as a pharmaceutical substance, to be applied to the surface of the dressing patch. This is in particular beneficial if the substance has a relatively short disintegration time, i.e. an integration time which is shorter than the durability of other parts or portions of the dressing product. Such a substance can advantageously be provided in a separate container, such as a tube, in which it does not disintegrate as fast as when contained in the dressing patch. Thanks to the opening in the protective sheet, the substance to be applied to the dressing product may be easily, but yet accurately, applied by an operator which in many instances is the patient himself/herself. The protective sheet may, in certain embodiments, adhere directly to the adhering surface of the dressing patch, whereas in other embodiments it may be otherwise connected thereto.

The at least one opening may be covered by a closing member which is separately releasable from the dressing patch in such a way that the at least one protective sheet remains attached to the dressing patch when the closing member is removed. Thereby, protection of that or those portions the dressing surface, which are accessible through the at least one opening, may be achieved until immediately before a substance is to be applied through the opening(s). Alternatively, or in addition, the protective sheet may define a folding line and two sections on either side of the folding line, with the first section adhering to the dressing, and the second section overlapping the first section. Accordingly, the second section may serve as a further protective sheet. For example, the cut-out section may be provided in the first section of the protective sheet, whereby the second section may protect that portion of the dressing surface which is accessible through the cut-out section. The folding line may define a hinge around which the second section may be flipped to lay open the opening for application of a pharmaceutical product to the dressing surface through the opening.

There may be provided only one or a plurality of openings, such as 2, 3, 4, 5-10, 11-15, 15-20 or more. The openings may be equidistantly arranged across a confined surface area of the at least one protective sheet, e.g. in an array pattern. In some embodiments, the plurality of openings are arranged in a circular fashion.

The at least one protective sheet may be comprised in a carrier system which comprises a gripping section which can be handled by human fingers and a dressing patch supporting section for applying the dressing patch to an application site. Examples of such carrier systems will be given below in connection with the description of the drawings.

The principle of the present invention works equally well in respect of relatively large dressings, i.e. wherein the surface area of the dressing patch is e.g. 5-20 $cm^2$ or more, or 10-20 $cm^2$, as in respect of relatively small dressings, i.e. wherein the surface area of the dressing patch is less than 5 $cm^2$, such as more than 2 $cm^2$ and less than 5 $cm^2$, such as 1-2 $cm^2$, such as 0.1-1 $cm^2$, such as less than 0.1 $cm^2$.

In some embodiments, in particular in those wherein the dressing patch constitutes a so-called thin film dressing, the adhering surface may essentially constitute the first surface of the dressing patch.

The above mentioned pharmaceutically active substances may be applied to the adhering surface of the dressing patch after completion of the adhering coating, or they may be mixed into the adhesive prior to coating thereof onto the backing layer, or they may otherwise be provided onto the surface of the dressing patch.

In case a foil or handgrip is attached or connected to the backing layer of the dressing sheet, there is preferably provided a further adhesive to the backing layer. The foil may, as an alternative to being provided at the backing layer side of the dressing sheet, be arranged between the adhering surface of the dressing sheet and the supporting sheet, preferably so that the foil is attached to a portion of the adhering surface of the dressing sheet and the supporting sheet adheres to the remaining portion of the adhering surface. An adhesive may be provided for securing an upper surface of the supporting sheet to a lower surface of the foil. The foil may define a hinge or folding line between to sections thereof, on of which adheres to the dressing sheet, allowing an operator, once the supporting sheet has been removed, to separate the foil from the dressing sheet by applying a pull to that section of the foil which does not adhere to the dressing sheet, so as to peel the foil off the sheet.

Accordingly, it is desirable that the hinge or folding line faces a central area of the dressing sheet, so that the peeling pull can be applied in a radial direction away from the central area of the dressing sheet. Preferably, the force needed for separating the foil from the dressing sheet is smaller than the force needed for separating the adhering surface of the dressing sheet from the application site, such as the skin of a human. The thus required releasability of the foil may be controlled by appropriate selection of a material of the foil or of a coating thereof, such as for example a silicone coating. In order to facilitate peeling of the foil and thus application of the dressing sheet, the foil may be flexible, i.e. with a bending stiffness which is normally smaller than the bending stiffness of the supporting sheet but yet greater than the bending stiffness of the dressing sheet.

The invention further relates to a dressing product comprising:
- a dressing sheet, one first surface of which is provided with an adhesive, whereby said first surface defines an adhering surface for attaching the dressing sheet to an anatomical surface of a living being;
- a carrier system defining a gripping section for handling of the carrier system by human fingers, the carrier system providing a support for the dressing sheet, wherein the carrier system defines a cavity for accommodating the dressing sheet.

Within the scope of the present invention there is further provided embodiments in which the carrier system defines a cavity for accommodating the dressing sheet, there being optionally provided a lid or cover sheet for the cavity in order to protect the adhering surface of the dressing sheet which faces towards the opening of the cavity. In one embodiment, the carrier system is made essentially from a blister material which is sufficiently flexible for allowing the dressing sheet to be applied by a finger tip pressure on a back surface of the carrier system when the carrier system is pressed against the anatomical surface at the application site.

The adhering surface preferably comprises hydrocolloid particles, the thickness of the adhesive being in the range of 25-300 μm, such as 30-200 μm, such as 25-150 μm, such as 30-100 μm, and the vapour permeability of the dressing sheet preferably being 200-2000 $g/m^2$, such as 200-1000 $g/m^2$, such as 300-800 $g/m^2$, such as 400-700 $g/m^2$, such as 450-650 $g/m^2$. It has been found that a dressing sheet with such thickness and vapour permeability provides a non-occlusive adhesive dressing sheet, i.e. one that enables moisture on, e.g., a skin surface to evaporate through the dressing sheet, so as to prevent undesired accumulation of moisture which could cause the dressing sheet to loose its adhering contact to the skin or promote bacterial growth between the sheet and the skin. Moreover, the small thickness of the dressing sheet results in a discrete appearance once applied to the application site.

The outer periphery of the dressing sheet may be bevelled in order to reduce the risk of rolling-up the dressing that would reduce wear-time. The edge is e.g. bevelled so that the thickness adjacent to the edge does not exceed about 30% of the maximum thickness of the dressing, more preferably not exceeding 25% of the maximum thickness for dressing having a miximum thickness above about 0.7 mm, whereas the thickness adjacent to the edge for dressings having maximum thickness below approximately 0.5 mm preferably does not exceed about 50% of the maximum thickness of the dressing sheet.

In order to result in a discrete appearance of the dressing when applied, e.g., to a face portion of a patient, the dressing sheet may be transparent.

Though the term adhesive is used herein it is understood that the term may cover any substance having adherent properties, such as adhesives, silicone or rubbery substances, petrolatum or the like, and hydrocolloid adhesives. The adhesive may be a pressure sensitive adhesive of any suitable kind known per se.

The supporting sheets of the various carrier systems, including those made from an optionally silicone coated paper, cardboard or plastics material may typically have a thickness of 0.1-1 mm, and the protective sheets, foils and foil members may typically have a thickness of 0.01-1.0 mm, such as 0.02-1.0 mm.

The invention further relates to a dressing product comprising:
- a dressing sheet, one first surface of which is provided with an adhesive, whereby said first surface defines an adhering surface for attaching the dressing sheet to an anatomical surface of a living being;
- a carrier system defining a gripping section for handling of the carrier system by human fingers, the carrier system comprise a protective sheet providing a support for the dressing sheet, and wherein the carrier system comprises a thread arranged between said adhering surface of the dressing sheet and the protective sheet and extending beyond a bound of the dressing sheet.

The dressing sheet is lifted off the protective sheet by pulling the threat away from the protective sheet, preferably in a substantially perpendicular direction of the protective sheet. The dressing sheet and thread is then applied to the skin, and the thread is subsequently removed by pulling in a direction being substantially parallel to the skin and dressing surface.

Preferably, in all embodiments of the present invention, the dressing sheet is provided in the form of a polyurethane film constituting a backing layer with an adhesive applied to one surface thereof. The backing layer may alternatively be of a non-woven material, a foam, PE or PVC. The adhering surface of the dressing sheet may comprise a pharmaceutically active substance. For example, emollients or e.g. retinoids for treating or preventing formation of psoriasis, eczema, callous, skin, corns or blisters. Examples of applicable pharmaceutical medicaments include a cytochine, such as a growth hormone or a polypetide growth factor such as TGF, FGF, PDGF, EGF, IGF-1, IGF-2, colony stimulating factor, transforming growth factor, nerve stimulating growth factor and the like giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorhexidine, silver salts such as sulphadizine, silver nitrate, silver acetate, silver lactate, silver sulphate, silver sodium thiosulphate or silver chloride, zind or salts thereof rnetronidazol, sulpha drugs, and pencillins, tissue-healing enhancing agents, e.g. RGD tripeptides and the like, proteins, amino acids such as taurine, vitamins such as ascorbic acid, enzymes for cleansing of wounds, e.g. pepsin, trypsin and the like, proteinase inhibitors for use in e.g. surgical insertion of the dressing in cancer tissue and/or other therapeutic agents which optionally be used for topical application, pain relieving agents such as lidocaine or chinchocaine, emollients, retinoids or agents having a cooling effect.

Due to its discrete appearance and the easy applicability provided by the carrier system, the dressing of the invention may advantageously be used for facial application, such as for the treatment of herpes, acne and warts with medicaments known per se for such purposes being contained in the adhesive or being applied thereto. Suitable anti viral medicaments for the treatment of herpes may for example comprise aciclovir or penciclovir. Azelain acid or isotretinoin may be used in a medicament for the treatment of acne. In respect of the treatment of warts, a mitotic inhibitor, such as podophyllotoxin, is applicable. Warts and/or clavus may be treated by salicylic acid-based medicaments.

The above mentioned pharmaceutically active substances may be applied to the adhering surface of the dressing sheet after completion of the adhering coating, or they may be mixed into the adhesive prior to coating thereof onto the backing layer.

In a second aspect the invention provides a method of applying a dressing sheet of a dressing product according to the first aspect of the invention, with a protective sheet for protecting the adhering surface of the dressing sheet and with a cut-out section being provided in the protective sheet, through which the adhering surface of the dressing is accessible, the method comprising:

separating the protective sheet from the adhering surface of the dressing sheet;

attaching at least a portion of the adhering surface to said anatomical surface, and subsequently separating the carrier system from the dressing sheet.

A pharmaceutical substance may be applied to the adhering surface of the through said cu out portion of the protective sheet prior to separation of the protective sheet from the non-overlapping region of the adhering surface of the dressing sheet.

In a third aspect the invention provides a kit comprising a dressing product according to the first aspect of the invention and a pharmaceutical product comprising a substance applicable to the dressing sheet.

The invention also provides a method for preparing a dressing patch of a dressing product as disclosed herein, the method comprising:

applying a substance, such as a pharmaceutical substance as described above, to a confined surface portion of said first surface of the dressing patch through the at least one opening; and subsequently:

separating the at least one protective sheet from the patch.

The invention further provides a method of treating a dermal or mucosal affection, comprising the steps of preparing a dressing patch of a dressing product as disclosed herein, the method of preparing comprising:

applying a pharmaceutical substance to a confined surface portion of said first surface of the dressing patch through the at least one opening; and subsequently:

separating the at least one protective sheet from the patch, the method of treating comprising applying the dressing patch to an anatomical surface of a living being.

In a final aspect, the invention provides a kit comprising a dressing product as disclosed herein and a container containing a substance applicable to a surface portion of the first surface of the dressing patch. The substance may comprise an ointment or cream, gel, liquid, e.g. a liquid spray, the substance optionally containing a pharmaceutically active substance, such as any of the substances and medicaments mentioned above.

DETAILED DESCRIPTION

Figure 1:
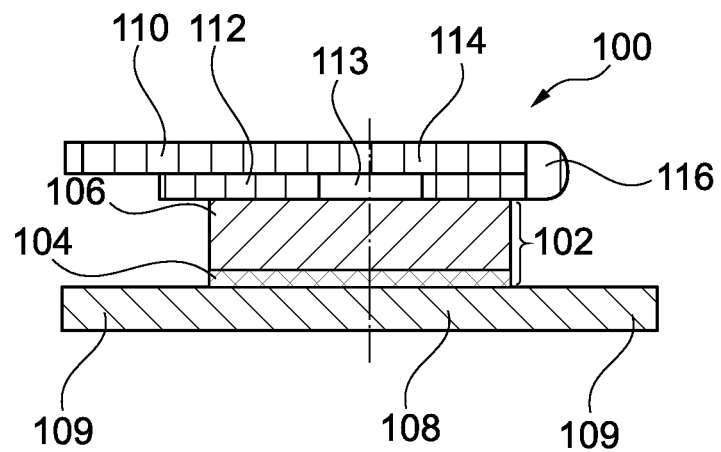
FIG. 1 is a cross-sectional view and FIG. 2 is a top view of one embodiment of a dressing product.

The invention will now be further described with reference to the drawings in which FIGS. 1-41 illustrate various embodiments of dressing products according to the invention.

It will be appreciated that the thicknesses of the various sheets, foils etc. of the carrier systems illustrated in the drawings are, for the purpose of clear illustration, drawn excessively large relative to the breadths and widths of such sheets, foils etc. In the shown embodiments, each dressing sheet 102 may have a total thickness some 50-350 µm or up to 1000 µm, whereas each of the carrier systems illustrated may have a width or breadth of typically 1-10 cm, preferably 1.5-6 cm.

Figure 2:
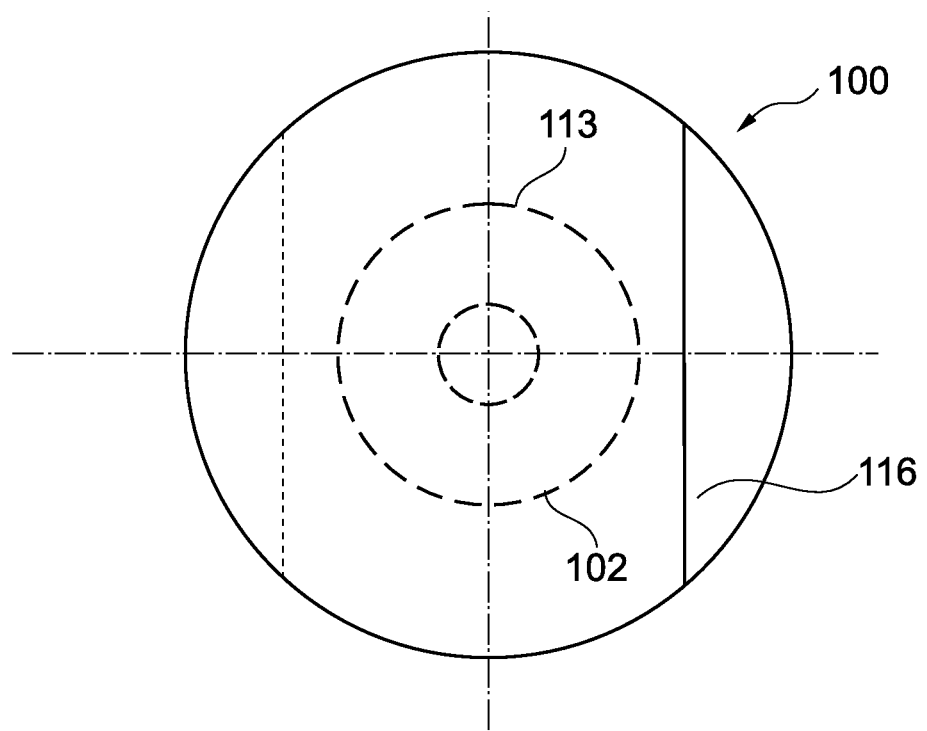

FIGS. 1 and 2 show a cross-sectional view and a top view, respectively, of a first embodiment of a dressing product 100. The dressing product comprises a dressing sheet 102 consisting essentially of a backing layer 104 made from e.g. polyurethane and coated with an adhesive 106, an adhering surface for attaching the dressing sheet to e.g. a skin portion of a patient being thereby defined by the upper surface of the adhesive 106. A carrier system is provided for supporting the dressing sheet 102 and for facilitating application thereof. The carrier system comprises a supporting sheet 108 made from a coated paper or cardboard material, and a foil member 110. A further adhesive (not shown) is provided for securing the supporting sheet 108 in relation to the backing layer 104. The supporting sheet 108 defines gripping sections 109 at the regions of non-overlap with the dressing sheet 102. The foil member 110 defines first and second sections 112 and 114, respectively, and a folding line or hinge 116. A cut-out section 113 is provided in the first section 112 of the foil member 110, so that a pharmaceutical substance may be applied to the adhering surface when the second section 114 is flipped away from the first section 112 around the hinge 116. The foil member may be peeled off the adhering surface and adhesive 106 by gripping the second section 114 and drawing it to the left in FIG. 1. The properties of the material of the surface of at least the first portion 112 of the foil 110 and the adhesive 106 on the one hand, and the material of the supporting sheet 108, the backing layer 104 and the adhesive (not shown) between the backing layer and the supporting sheet on the other hand are such that the dressing sheet 102 firmly sticks to the supporting sheet when the foil member 110 is peeled off the adhesive 106. An operator may then grip either one or both of the gripping sections 109 and apply the dressing sheet to an application site with the adhesive 106 facing the application site. Once the adhesive 106 adheres to the application site, the supporting sheet 108 is separated from the backing layer 104, the force being required therefor being smaller than the force required for separating the adhesive 106 from the application site, e.g. a skin portion of a human, so that it is ensured that the dressing sheet 102 firmly sticks to the application site when the supporting sheet 108 is removed. The embodiment of FIGS. 1 and 2 may be modified by enlarging the gripping sections 109 in order to provide an extended handling area.

Figure 3:
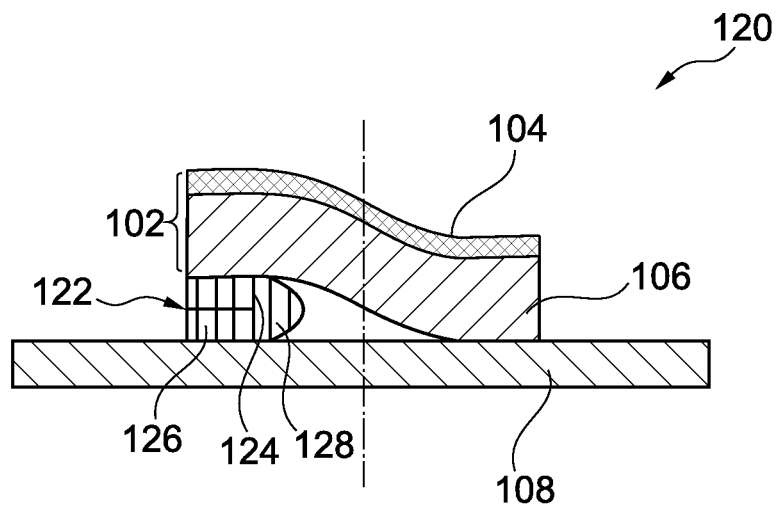
FIG. 3 is a cross-sectional view and FIG. 4 is a top view of one embodiment of a dressing product.
Figure 4:
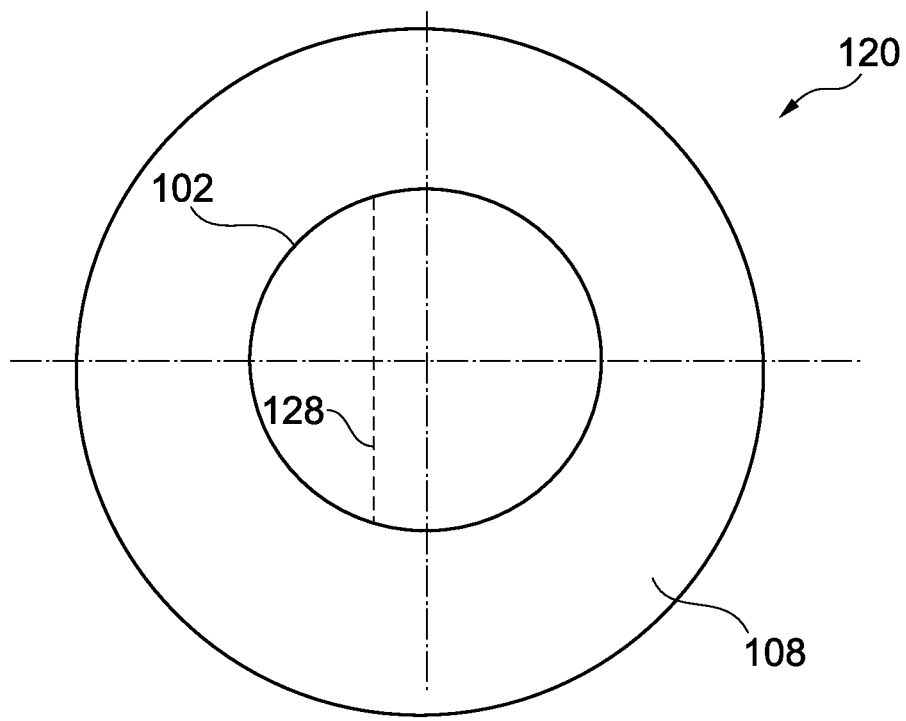

FIGS. 3 and 4 show a second embodiment of a dressing product 120, comprising dressing sheet 102 with backing layer 104 and adhesive 106. A foil member 122 is arranged between a portion of adhesive 106 and the supporting sheet 108, the foil member 122 defining first and second sections 124 and 126, respectively, which are interconnected at hinge or folding line 128. An adhesive (not shown) may be provided between a lower surface of the second foil section 126 and an upper surface of the supporting sheet 108. A cut-out section (not shown) may optionally be provided in the supporting sheet 108 in a region of non-overlap with the foil member 122, so that a pharmaceutical substance may be applied to the adhesive 106 through the cut-out section. Preferably, the cut-out section is provided so that the only a central portion, and not the periphery of the adhesive 106, is exposed through the cut-out section, whereby it may efficiently be prevented that pharmaceutical substance is applied to the periphery of the adhesive 106 which could comprise the adhering effect of the adhesive 106 once applied to the application site. Prior to use, the supporting sheet 108 is removed, with the foil 122 remaining attached to the adhesive 106. The second foil section 126 is then used as a gripping section for application of the dressing sheet 102. During application, a right-hand portion of the adhesive 106 is initially adhered to the application site, and the foil 122 is then gradually peeled off the adhesive 106, as the remaining portion of the adhesive 106 gradually contacts and adheres to the application site. The supporting sheet 108 of FIG. 3 may, for example, be made from a paper or cardboard material, optionally coated with e.g. a silicone material, or from PETP.

Figure 5:
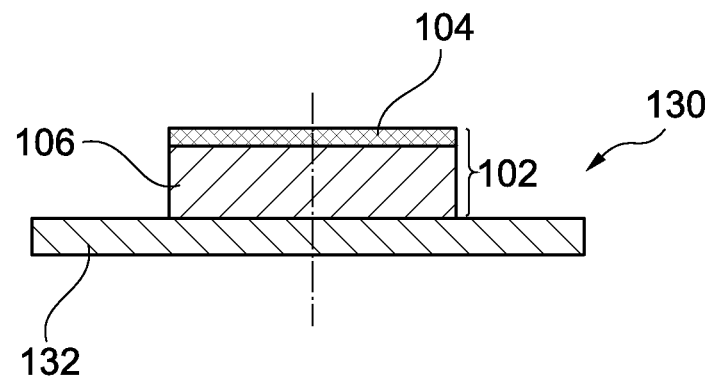
FIG. 5 is a cross-sectional view and FIG. 6 is a top view of one embodiment of a dressing product.
Figure 6:
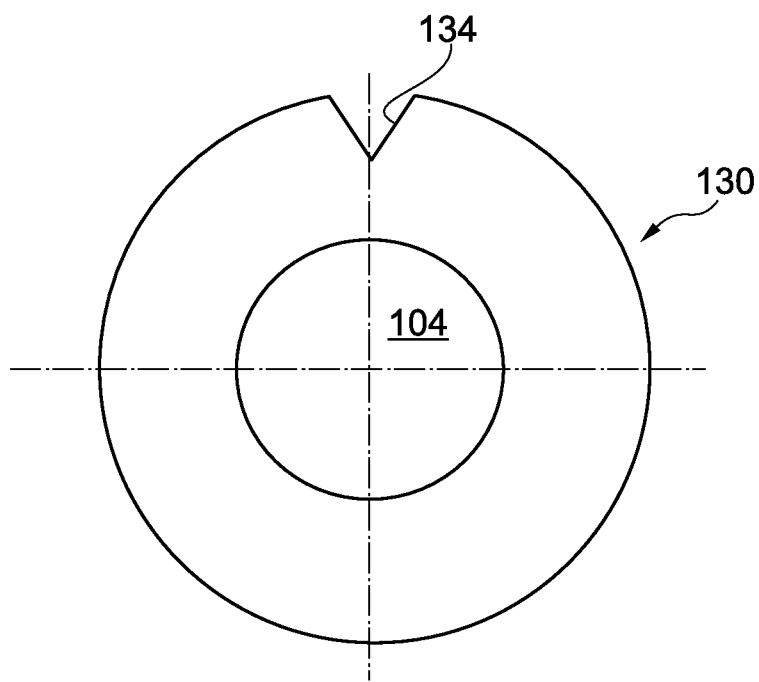

In the embodiment of FIGS. 5 and 6, a dressing product 130 comprises a supporting sheet 132, which, for example, may be made from PETP. The supporting sheet 132 defines a notch 134, whereby the carrier system may be broken when a tension is applied by an operator to the supporting sheet in the region of the notch 134. Prior to application of the dressing sheet 102, the supporting sheet 132 is broken at the notch 134, and a portion of the supporting sheet is twisted outwardly, so as to expose a portion of the adhesive 106, which portion is initially adhered to the application site. The supporting sheet 132 is the gradually separated from the adhesive, as the remaining portions of the adhesive gradually attach to the application site.

Figure 7:
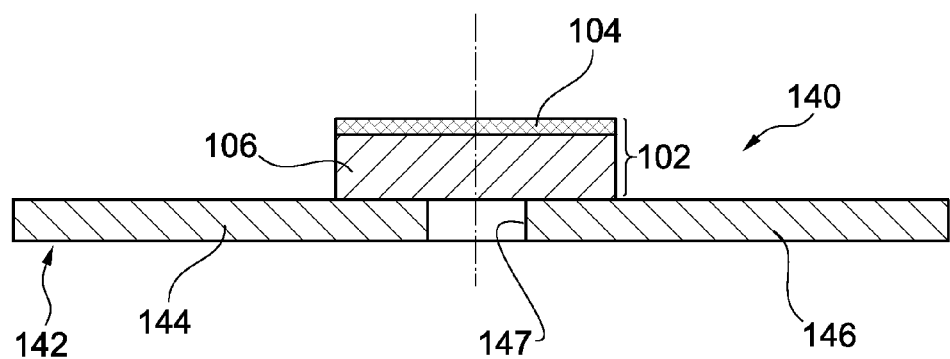
FIG. 7 is a cross-sectional view and FIG. 8 is a top view of one embodiment of a dressing product.
Figure 8:
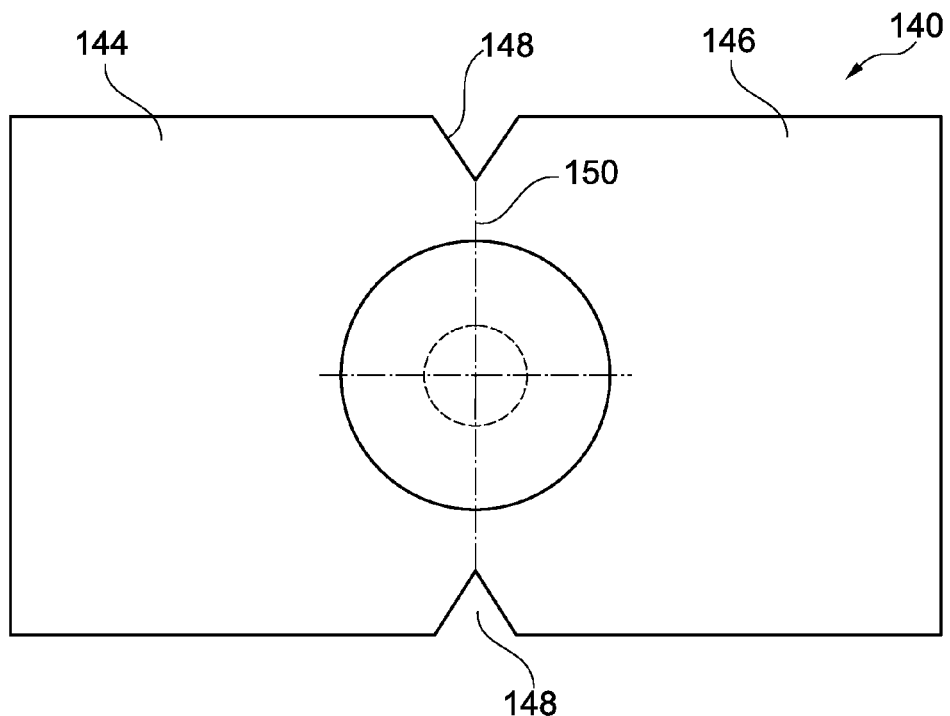

FIGS. 7 and 8 show a further embodiment of a dressing product 140 which comprises a carrier system 142 with a supporting section 144 and a protective sheet 146, which is integral with the supporting section 144. Two opposing notches 148 are provided at either side of the carrier system at the transition between the supporting section 144 and the protective sheet 146. A cut-out section 147, through which a pharmaceutical substance may be provided to the adhesive 106, is provided in the carrier system. Prior to application of the dressing sheet 102, the protective sheet 146 is torn off the supporting section 144 by braking the carrier system 142 between the notches 148, as indicated by dashed line 150 in FIG. 7. A right-hand portion of the adhesive 106 is then attached to the application site, and the supporting section is finally gradually separated from the adhesive 106, as the remaining sections of adhesive gradually attach to the application site. The supporting sheet may e.g. be made from PETP.

Figure 8A:
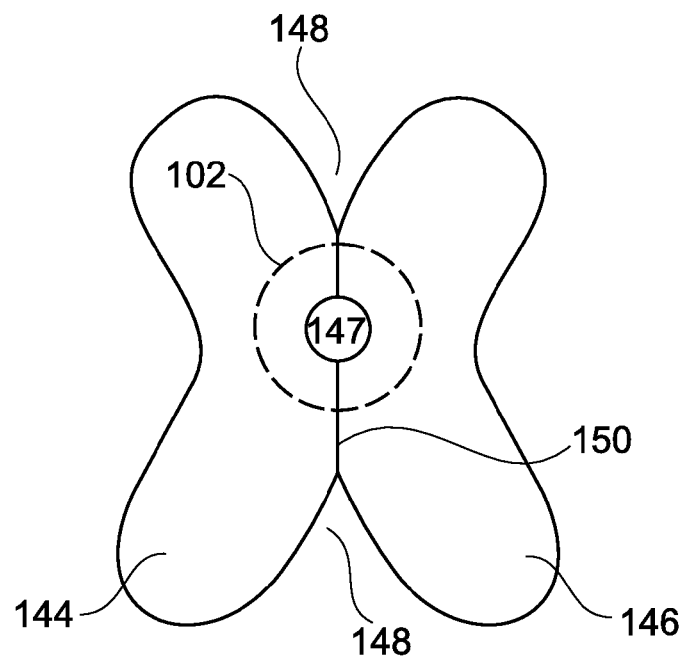
FIG. 8a is a bottom view of one embodiment of a dressing product and FIG. 8b illustrates the dressing product including a carrier system.

In FIG. 8a is shown another embodiment of a dressing product, seen from below. The dressing system comprises a carrier system with a supporting section 144 and a protective sheet 146, which is integral with the supporting section 144. The protective sheet and the supporting section have rounded corners and converge to the central part of the system rendering a "butterfly shape". Two opposing notches 148 are provided at either side of the carrier system at the transition between the supporting section 144 and the protective sheet 146. A cut-out section 147, through which a pharmaceutical substance may be provided to the adhesive, is provided in the carrier system. Prior to application of the dressing sheet 102, the protective sheet 146 is torn off the supporting section 144 by twisting the supporting section 144 and the protective sheet 146 along the connection line 150. The now exposed adhesive of the dressing sheet 102 is then attached to the application site, and the supporting section 144 is gradually separated from the adhesive, again by twisting the supporting section 144 with respect to the dressing sheet 102, as the remaining sections of adhesive gradually attach to the application site. The butterfly shape of the carrier system provides a good grip for the fingers during the twisting movement.

Figure 8B:
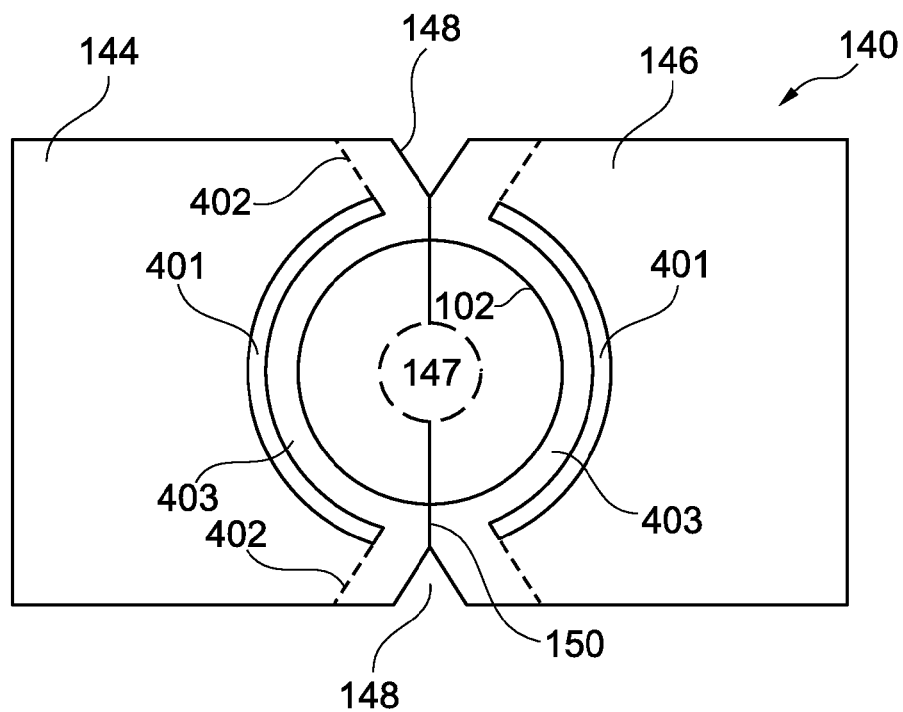

FIG. 8b shows a further embodiment of a dressing product 140, which comprises a carrier system in the form of a supporting section 144 and a protective sheet 146, which is integral with the supporting section 144. Two opposing notches 148 are provided at either side of the carrier system at the transition between the supporting section 144 and the protective sheet 146. A cut-out section 147, through which a pharmaceutical substance may be provided to the adhesive surface of the dressing sheet 102, is provided in the carrier system. The protective sheet 146 and the supporting section 144 are both provided with curved slits 401, being substantially coaxial to the cut-out section 147. At each end section of the slits 401 is provided a pre-bended line 402, shown as dashed line, extending from the end section of the slit 401 to the edge portion of the protective sheet 146 or the supporting section 144. The pre-bended lines 402 are preferably not parallel to the slit; more preferred they are substantially perpendicular to the slits.

Prior to application of the dressing sheet 102, the protective sheet 146 is torn off the supporting section 144 by pulling the supporting section 144 and the protective sheet 146 away from each other. When exposed to the pull force, the intermediate portions 403 of the protective sheet 144 and the supporting section 146 between the slit 401 and the cut-out section 147 will, due to the pre-bended lines 402 bend slightly upwards. This movement will ease the release of the dressing sheet 102 from the protective sheet 144 and the protective sheet 144 is finally gradually separated from the adhesive of the dressing sheet. This operation may be done without twisting the construction 140, which otherwise may be done to separate the protective sheet and the supporting section. Twisting at this stage may give rise to undesired folding or stretching of the dressing sheet. Now the dressing sheet 102 is attached to the supporting section 146 and the dressing sheet 102 is brought into contact with the desired application site. When the exposed part of the adhesive of the dressing sheet is fixed to the application site, the supporting section is pulled away. Again the intermediate portion 403 will bend and rise, and ease the release of the dressing sheet 102. Again, no twisting is needed, and the dressing is applied smooth and without wrinkles. The slits 401, combined with the pre-bended lines 402, provide an easy and uncomplicated transfer of the dressing sheet from the support to the application site.

Figure 9:
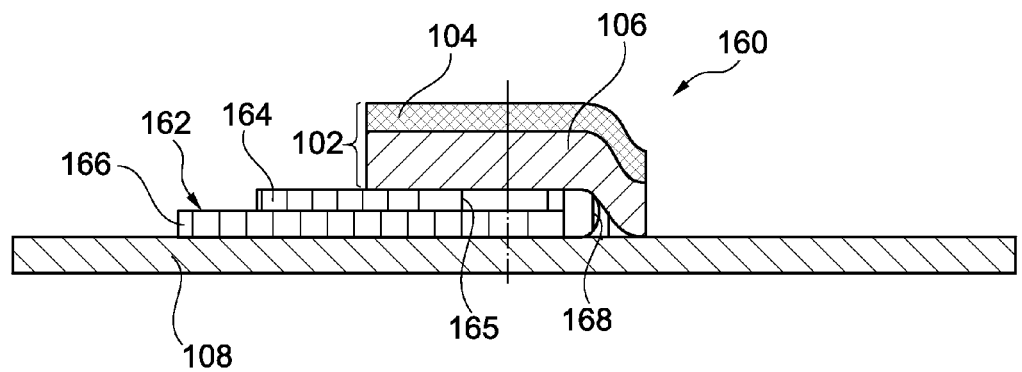
FIG. 9 is a cross-sectional view and FIG. 10 is a top view of one embodiment of a dressing product.
Figure 10:
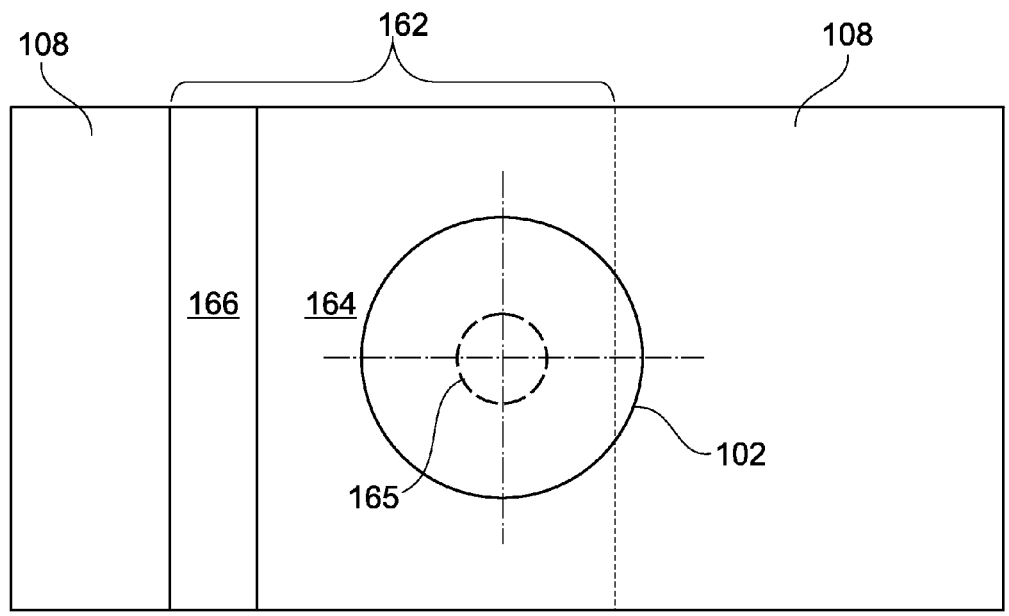

A further embodiment of a dressing product 160 is shown in FIGS. 9 and 10, in which a foil member 162 is arranged between supporting sheet 108 and a portion of the adhesive 106. The foil member defines first and second sections 164 and 166, respectively, at the transition between which there is defined a hinge or folding line 168. An adhesive (not shown) is optionally provided for adhering a lower surface of the second foil section 166 to an upper surface of the supporting sheet 108. Prior to application of the dressing sheet 102, the supporting sheet 108 is separated from the adhesive 106 and the second foil section 166, which in turn is flipped around hinge or folding line 168, whereby a portion of the adhesive 106 is exposed through cut-out section 165, through which a pharmaceutical substance may be applied. An initial portion of the adhesive 106 (to the right in FIG. 9) is then adhered to the application site, and as the foil member 162 is gradually peeled off the adhesive 106, the remaining portions of the adhesive 106 gradually adhere to the application site.

Figure 11:
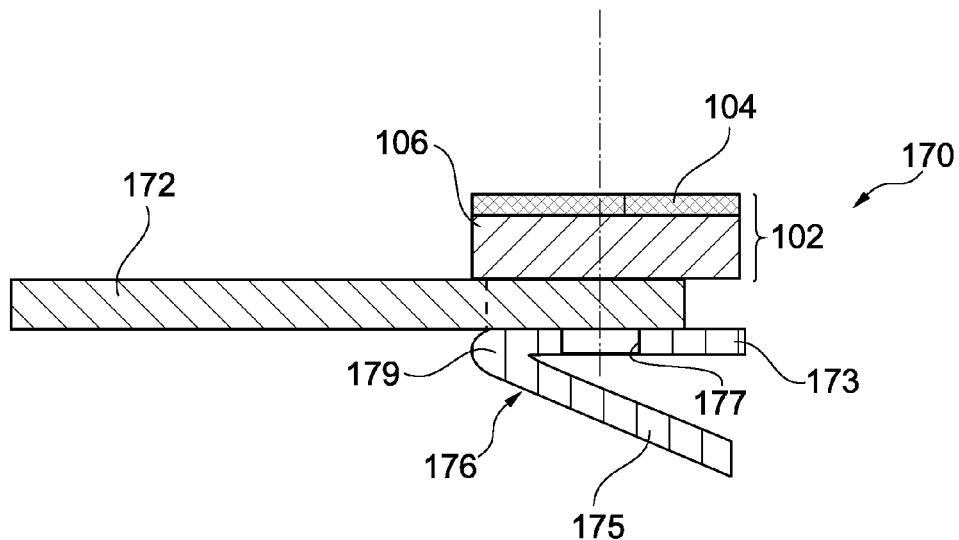
FIG. 11 is a cross-sectional view and FIG. 12 is a top view of one embodiment of a dressing product.
Figure 12:
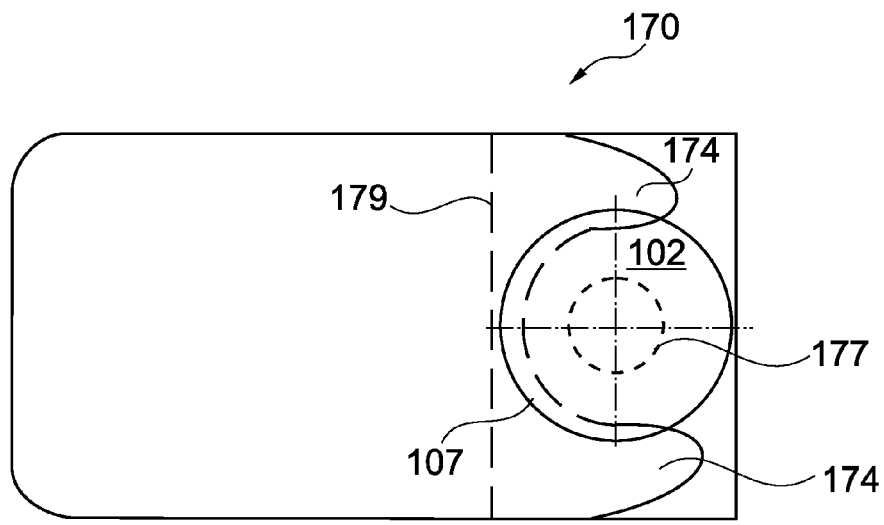

FIGS. 11 and 12 show a further embodiment of a dressing product 170. The carrier system of the dressing product comprises a sheet supporting section 172 defining a U-shaped and portion 174 with legs of the U defining a support for a peripheral section 107 of the adhesive 106. A protective sheet or foil member 176 adheres to a lower portion of the supporting section 172 by means of adhesive 178. Though the protective sheet 176 does not contact the adhesive 106 in FIG. 11, it will be appreciated that, due to the flexibility of the protective sheet 176 and dressing sheet 102, the protective sheet will normally adhere to the adhesive 106, whereby improved protection of the adhesive 106 is achieved. The protective sheet 176 may define a cut-out section 177 through which a pharmaceutical substance may be applied to a central portion of the adhesive 106 prior to application of the dressing sheet. The protective sheet 176 defines first and second sections 173 and 175, respectively overlapping each other and being interconnected at a hinge or folding line 179, whereby lower section 175 protects that part of the adhesive 106, which is exposed through cut-out section 177. An adhesive (not shown) is applied not only in the region in which the protective sheet 176 overlaps the supporting section 172, but also in the region in which the protective sheet 176 overlaps the dressing product 102 and thereby the adhesive 106. It should, however, be understood that the adhesive need not be provided in the region of overlap with the dressing product, as the adhesive 106 thereof may serve to adhere the protective sheet 176 to the dressing product. Prior to application of the dressing sheet 102, the protective sheet 176 is peeled off the dressing product 102 and off the supporting section 172. An operator holding the supporting section 172, which also constitutes a gripping section of the carrier system, then attaches the adhesive 106 to the application site, and once those portions of the adhesive, which do not constitute the peripheral section 107, are attached to the application site, the supporting sheet 172 is peeled off the peripheral section 107 of the adhesive 106 by simultaneously twisting the supporting section 172 away from the application site (upwardly in FIG. 11) and drawing it away from the dressing sheet (to the left in FIG. 11). The supporting section 172 may e.g., be made from a silicone coated cardboard, paper or plastics material, such as PETP.

Figure 13:
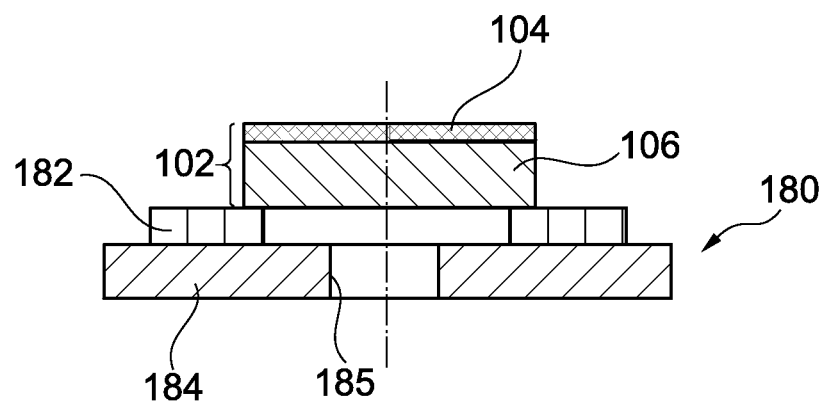
FIG. 13 is a cross-sectional view and FIG. 14 is a top view of one embodiment of a dressing product.
Figure 14:
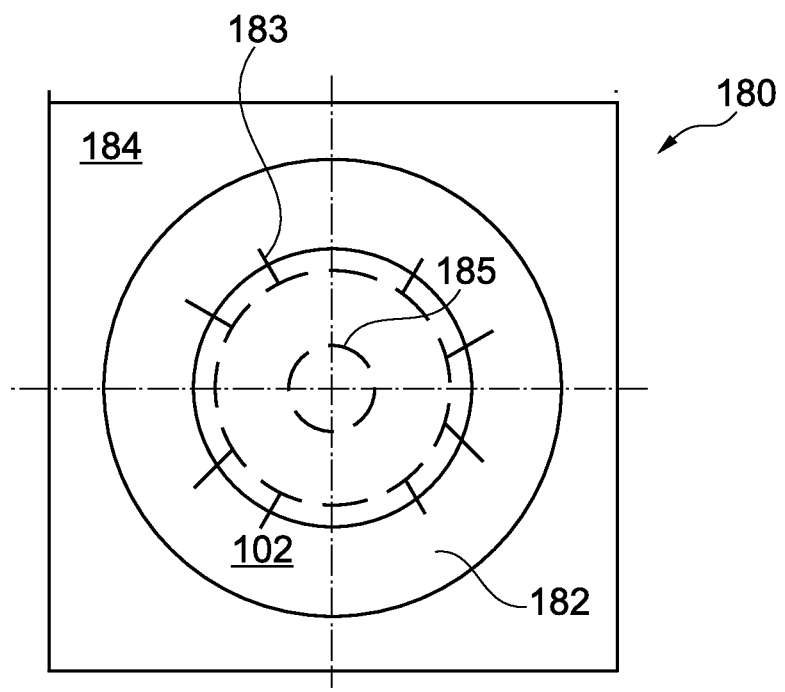

In the embodiment of FIGS. 13 and 14 of a dressing product 180, the carrier system comprises a ring-shaped sheet 182 and supporting section 184 which may adhere to the ring-shaped sheet by and adhesive (not shown). As shown in FIG. 14, the ring-shaped sheet 182 defines a plurality of radially extending slits or notches 183 which are preferably equidistantly arranged along an inner periphery of the sheet 182. However, the slits 183 may alternatively be arranged along the outer periphery of the sheet 182, or slits may be arranged at the inner as well as at the outer periphery. A cut-out section 185 of the supporting section 184 allows for application of a pharmaceutical substance to the adhesive 106. Prior to application of the dressing product, the supporting section 184 is separated from the ring-shaped sheet 182. Next, the ring-shaped sheet 182 is broken at one or more of the slits 183, so that an initial portion of a periphery of the adhesive 106 is exposed and ready for application. Once such an initial portion of the periphery of the adhesive 106 adheres to the application site, the remaining portions thereof are gradually attached to the application site as the sheet 182 is gradually peeled of the adhesive 106, whereby the sheet 182 will normally brake at several or all of the slits 183. The supporting section 184 may e.g. be made from a PETP foil, optionally coated with e.g. a silicone material, and for convenient control of release values, the ring-shaped sheet 182 may be silicone coated.

Figure 15:
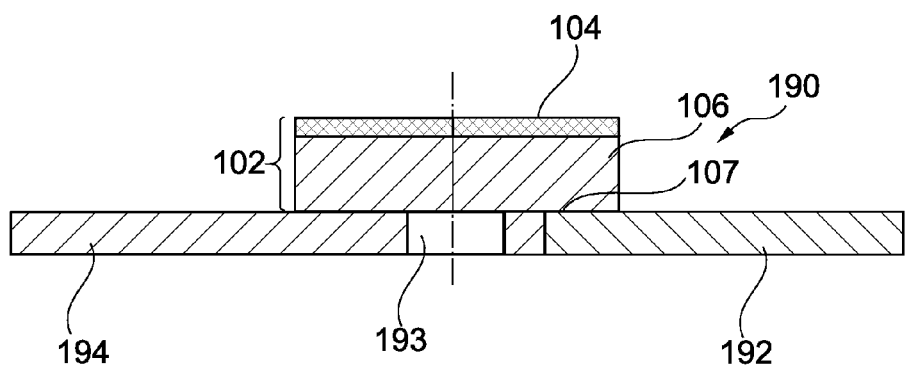
FIG. 15 is a cross-sectional view and FIG. 16 is a top view of one embodiment of a dressing product.
Figure 16:
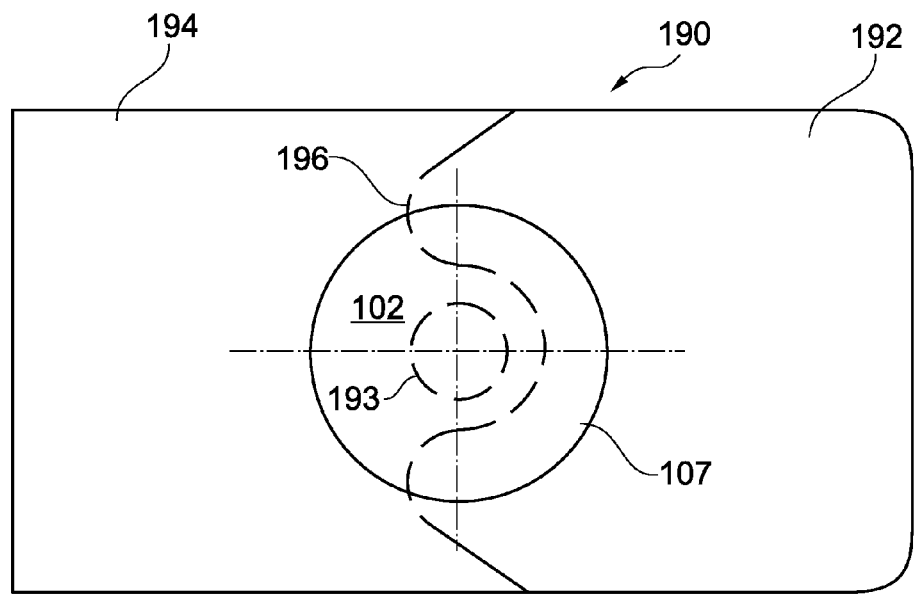

The carrier system of the embodiment of a dressing product 190 shown in FIGS. 15 and 16 comprises a supporting section 192, which also defines a gripping section, and a protective sheet 194, which is provided with a cut-out section 193. Preferably, the section 192 and sheet 194 are made from the same sheet material and separated by a cut or punching along line 196. That end portion of section 192 which faces sheet 194 is essentially U-shaped, with the facing end portion of sheet 194 defining a complementary shape. The dressing sheet 102 is arranged at the transition between section 192 and sheet 194 and may serve to secure section 192 in relation to sheet 194. Alternatively or additionally, a separate adhesive-coated sheet (not shown) may be provided for securing section 192 in relation to each other. Prior to application of the dressing sheet 102, the sheet 194 is separated from the dressing sheet 102 by twisting it out of the plane of FIG. 15 and drawing it away from the supporting section 192. The legs of the U-shaped end portion of the supporting section 192 thereby define a support for the peripheral section 107 of the dressing sheet 102. A pharmaceutical product may be applied to the adhering surface of the dressing product 102 which is exposed between the two legs of the U-shaped and portion of the supporting sheet 192. The dressing sheet 102 is applied to the application site by the supporting and gripping section 192 which is peeled off the dressing sheet once the non-supported portion of the dressing sheet adheres to the application site, whereby the peripheral section 107 may finally adhere to the application site. The section 192 and sheet 194 may have different release properties, so that a larger force is required for separating the dressing sheet 102 from the supporting section 192 than the force needed for separating the sheet 194 from the dressing sheet 102, whereby it may be ensured that the dressing product sticks to supporting section 192 (and not to sheet 194) when the section 192 and sheet 194 are separated. This effect may be achieved by different surface materials of the section 192 and of the sheet 194, e.g. by coatings of different silicone materials. The aforementioned effect may alternatively be achieved—or enhanced—by designing the supporting section 192 and the sheet 194 such that a major part of the surface area of the dressing sheet 102 adheres to the sheet 194.

Figure 17:
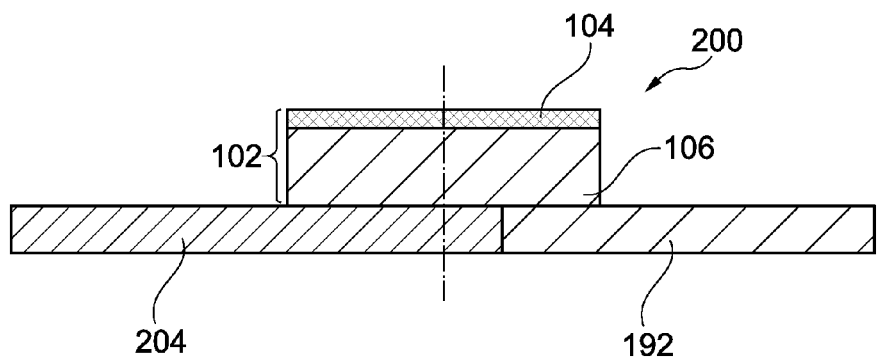
FIG. 17 is a cross-sectional view and FIG. 18 is a top view of one embodiment of a dressing product.
Figure 18:
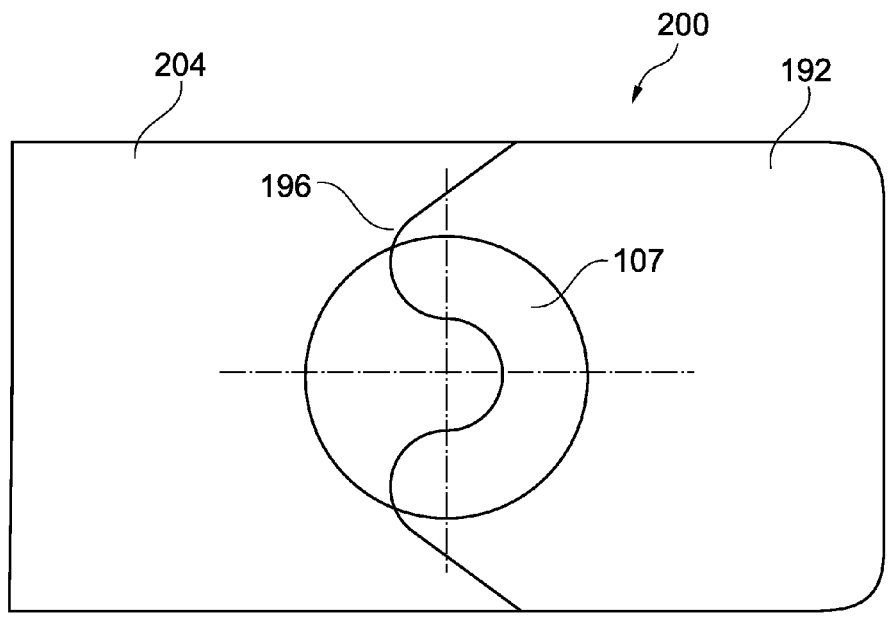

A similar embodiment is shown in FIGS. 17 and 18, in which dressing product 200 comprises a protective sheet 204 essentially identical to the protective sheet 194 of the embodiment of FIGS. 15 and 16, but with no cut-out section being provided therein. The remaining elements of FIGS. 17 and 18 are the same as those of the embodiment of FIGS. 15 and 16 and are thus referred to by the same reference numerals as in FIGS. 15 and 16.

Figure 19:
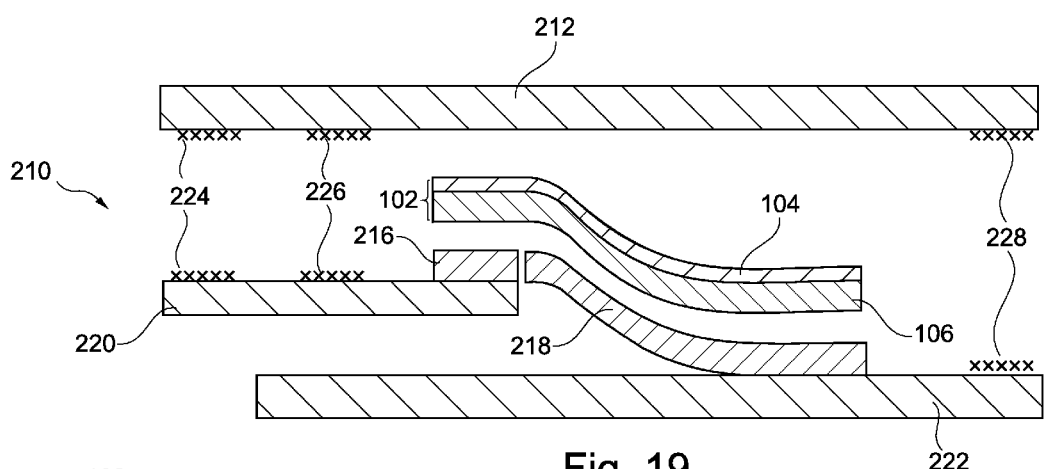
FIGS. 19 and 20 are cross-sectional views of one embodiment of a dressing product.
Figure 20:
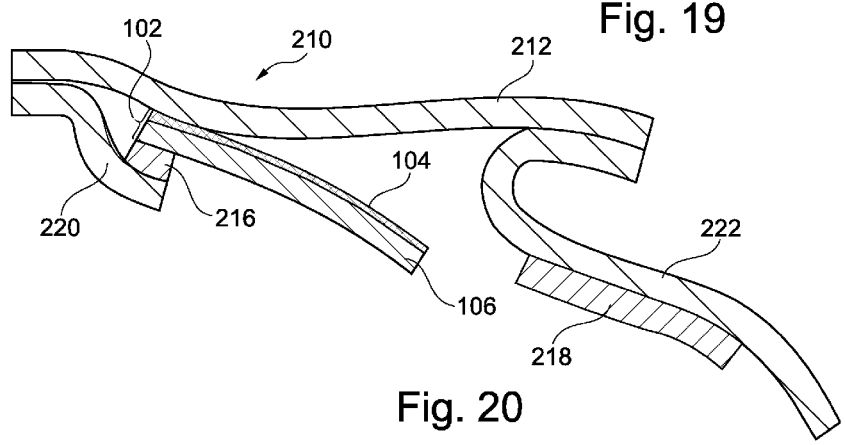

FIGS. 19 and 20 illustrate yet a further embodiment of a dressing product 210, the carrier system of which comprises a supporting sheet 212, first and second protective sheets 216 and 218, respectively, intermediate sheet 220 and cover sheet 222. Supporting sheet 212 is secured to intermediate sheet 220 at welding portions 224 and 226 and to cover sheet 222 at welding portion 228. Cover sheet 222 is secured to intermediate sheet 220 at welding portion 230. FIG. 20 shows a configuration of the dressing product 210 which occurs during application thereof. Cover sheet 222 has been separated from intermediate sheet 220 by braking welding 230, and protective sheet 218 has been peeled off adhesive 106. Backing layer 104 has been partially peeled off supporting sheet 212, there being optionally provided an adhesive (not shown) for fixing the backing layer to the supporting sheet 212. Once the adhesive 106 has been applied to the application site, protective sheet 216 is peeled off the adhesive. The protective sheets 216 and 218, which may be made from a continuous sheet of material, which is cut or punched to establish two distinct sheets, may e.g. be made from a silicone coated PETP sheet. The supporting sheet 212, intermediate sheet 220 and cover sheet 222 may e.g. be made from foil of a plastics material.

Figure 21:
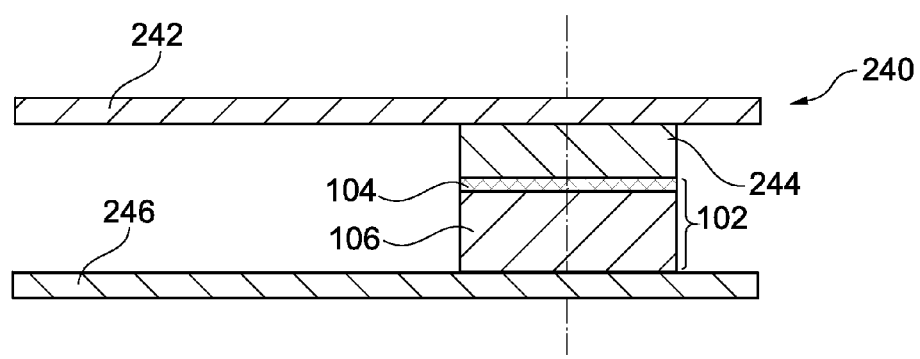
FIG. 21 is a cross-sectional view and FIG. 22 is a top view of one embodiment of a dressing product.
Figure 22:
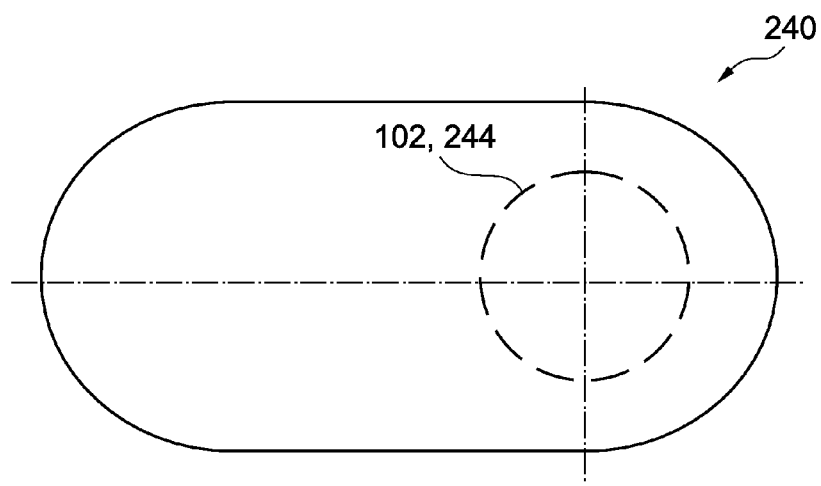

In the embodiment of FIGS. 21 and 22, the carrier system of a dressing product 240 comprises a combined supporting and gripping sheet 242 connected to backing layer 104 of the dressing sheet 102 via intermediate layer 244. A protective sheet 246 adheres to the adhesive 106. An adhesive (not shown) may be applied to either of the two surfaces of intermediate layer 244. Prior to application of the dressing sheet 102, the protective sheet, which may e.g. be made from a silicone coated PETP foil, is separated from the dressing sheet 102. Preferably the adhering properties of the materials and adhesives used are such that the force required for separating the protective sheet 246 from the adhesive 106 is smaller than the force needed for separating the backing layer 104 from the intermediate layer 244. The intermediate layer 244, which may e.g. be made from a paper or cardboard material, ensures a predetermined distance between the lower surface of the supporting sheet 242 and the application site for facilitating application of the dressing product 102 which is applied by means of the supporting sheet 242 once the protective sheet 246 has been removed.

Figure 23:
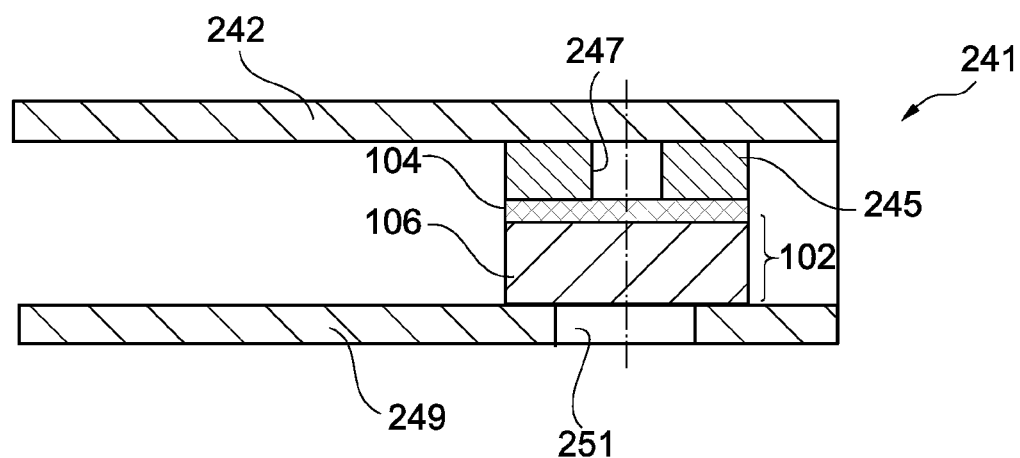
FIG. 23 is a cross-sectional view and FIG. 24 is a top view of one embodiment of a dressing product.
Figure 24:
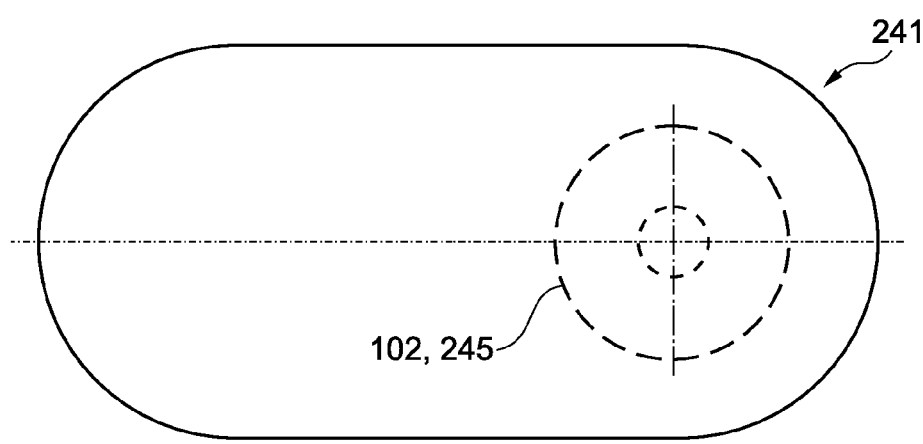

The embodiment of a dressing product 241 of FIGS. 23 and 24 is a slightly modified version of the embodiment of FIGS. 21 and 22. A cut-out section 247 is provided in intermediate layer 245, and a cut-out section 251 is provided in protective sheet 249 for application of a pharmaceutical substance to the adhesive 106. When the dressing sheet 102 with a pharmaceutical product, which may e.g. be in the form of a cream, is pressed against the application site, the dressing product may deflect slightly into the cut-out section 247 of intermediate layer 245, whereby mashing of the cream onto the peripheral section of the adhesive 106 may be prevented or reduced.

Figure 25:
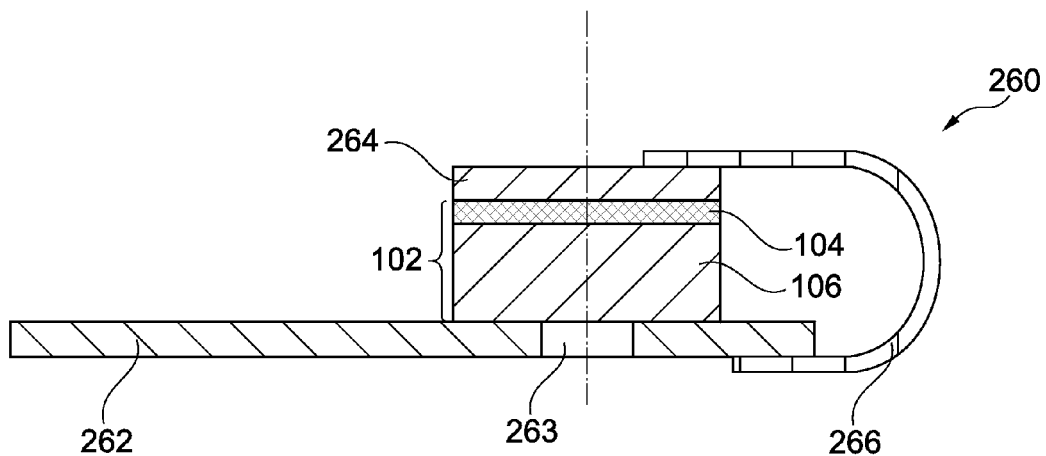
FIG. 25 is a cross-sectional view and FIG. 26 is a top view of one embodiment of a dressing product.
Figure 26:
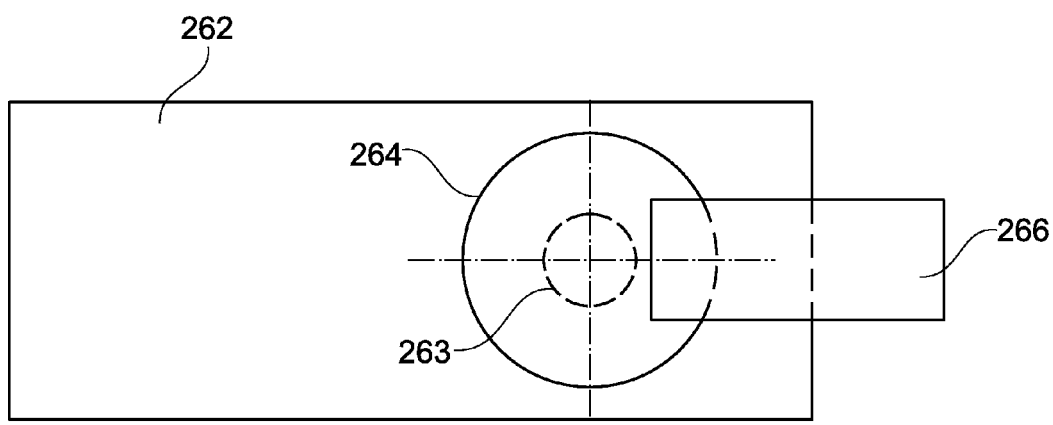

FIGS. 25 and 26 illustrate an embodiment of a dressing product 260, the carrier system of which comprises a combined supporting and gripping sheet 262 connected to a sheet 264 via hinge member 266. A cut-out section 263 is provided in the supporting sheet 262. The adhesive 106 may be released from the supporting sheet 262 and flipped over by means of the hinge member 266, whereby the hinge member 266 and the dressing sheet 102 may form an extension of the supporting sheet 262 in the cross-sectional view of FIG. 25. When the dressing sheet is applied to the application site, the sheet 264, which may be attached to the backing layer 104 by means of an adhesive (not shown), separates from the backing layer 104. The sheet 264 may be made from a paper or cardboard material, and the supporting sheet 262 may e.g. be made from a PETP foil.

Figure 27:
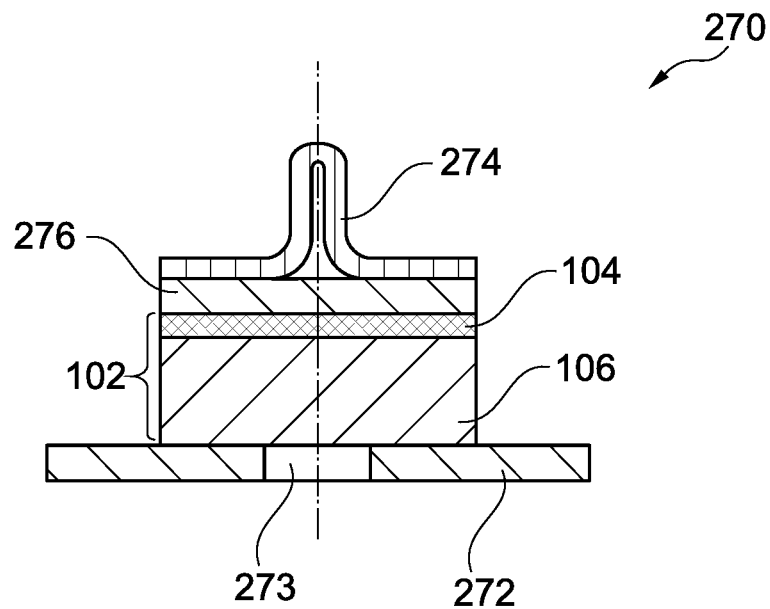
FIG. 27 is a cross-sectional view and FIG. 28 is a top view of one embodiment of a dressing product.
Figure 28:
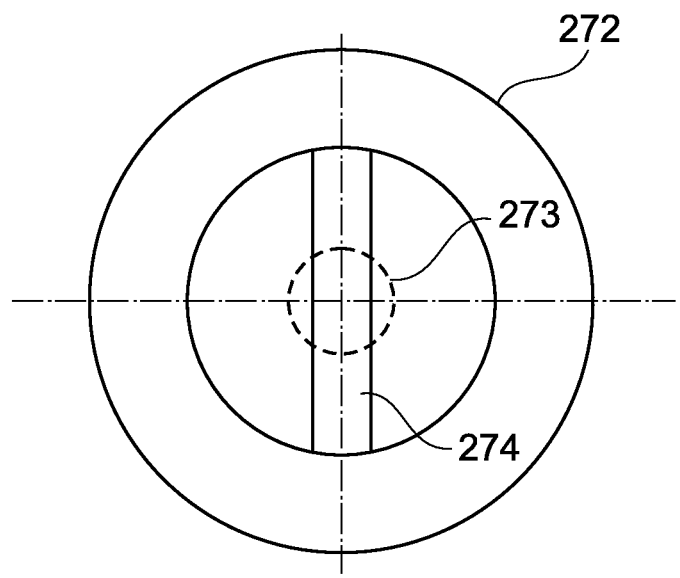

In the embodiment of a dressing product 270 of FIGS. 27 and 28, the carrier system comprises a protective sheet 272 with a cut-out section 273, a handgrip member 274 and an intermediate paper or cardboard layer 276 attached to the backing layer 104 by an adhesive (not shown). When the protective sheet 272 has been separated from the dressing sheet 102, the latter may be applied to the application site by means of the handgrip member 274, the paper layer 276 separating from the backing layer 104 once the adhesive 106 adheres to the application site and the handgrip member 274 is withdrawn. The protective sheet 272 may e.g. be made from a PETP sheet.

Figure 29:
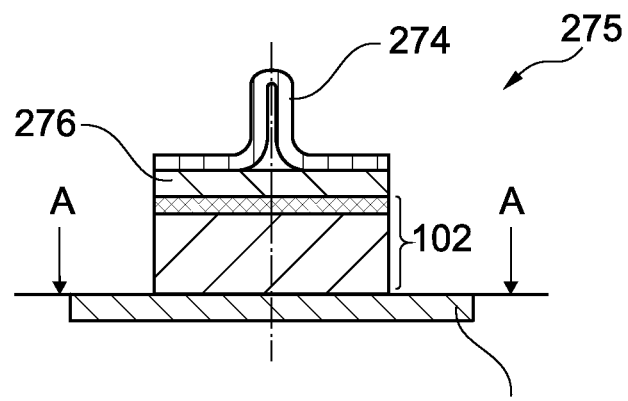
FIG. 29 is a cross-sectional view and FIG. 30 is a top view of one embodiment of a dressing product.
Figure 30:
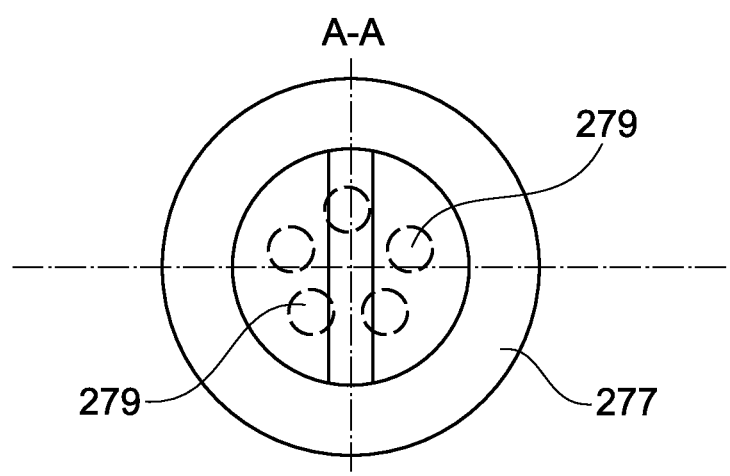

FIGS. 29 and 30 show an embodiment similar to the embodiment of FIGS. 27 and 28, in which dressing product 275 comprises a protective sheet 277 with a plurality of openings or cut-out sections 279, see FIG. 30 in which five such cut-out sections are depicted.

Figure 31:
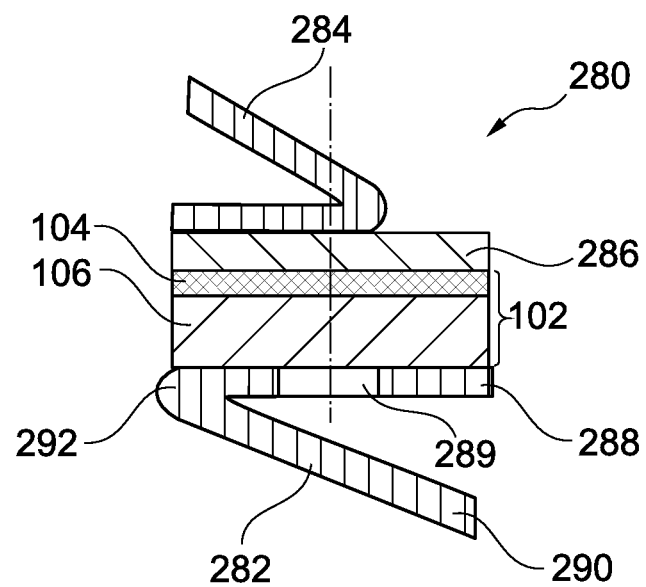
FIG. 31 is a cross-sectional view and FIG. 32 is a top view of one embodiment of a dressing product.
Figure 32:
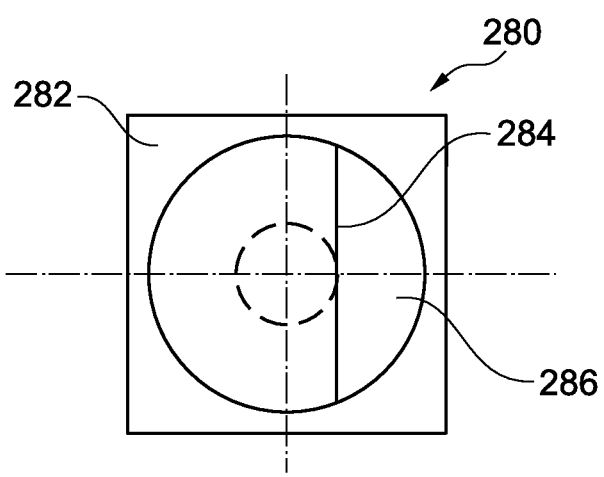

A similar embodiment is shown in FIGS. 31 and 32. The carrier system of a dressing product 280 comprises a protective sheet 282 having first and second overlapping sections 288 and 290, respectively, which are interconnected at hinge or folding line 292, a folded gripping section 284 and a paper or cardboard layer 286. A cut-out section 289 is provided in the first sheet section 288 and covered by the second sheet section 290 in the initial condition of the sheet. Once the second section 290 has been flipped over, and the first section has been peeled off the adhesive 106, the gripping sheet 284 is used to apply the dressing sheet 102 to the application site.

Figure 33:
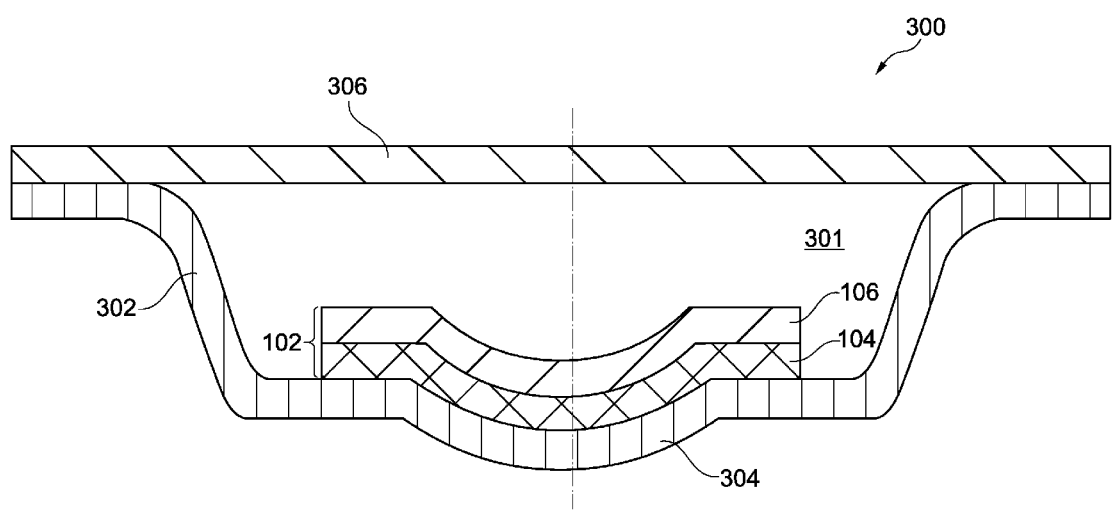
FIG. 33 is a cross-sectional view of one embodiment of a dressing product.
Figure 34:
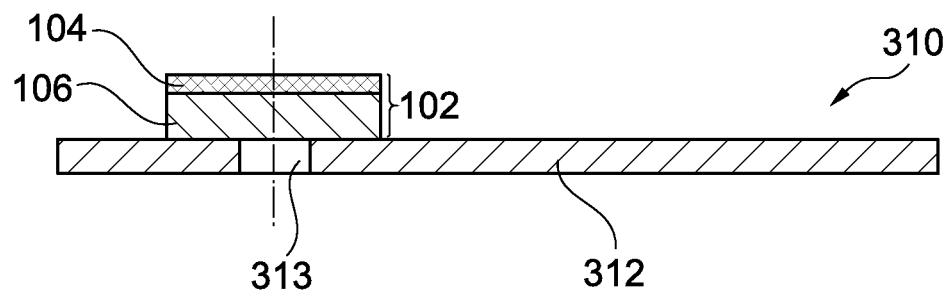
FIGS. 34 and 37 are cross-sectional views.
Figure 35:
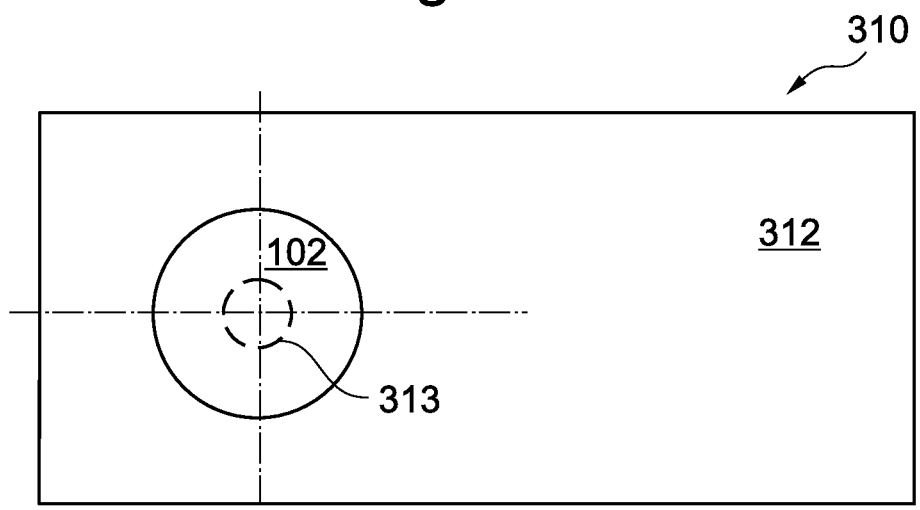
FIG. 35 is a top view.

In the embodiment of the dressing product 300 of FIG. 33, the carrier system defines a cavity 301 for accommodating the dressing sheet 102, there being provided a lid or cover sheet 306 for the cavity 301 in order to protect the adhesive 106 of the dressing sheet 102. A lower part 302 of the carrier system is essentially made from a blister material which is sufficiently flexible for allowing the dressing sheet 102 to be applied by a finger tip pressure on a back surface of the blister material at the region of protruding portion 304.

Figure 36:
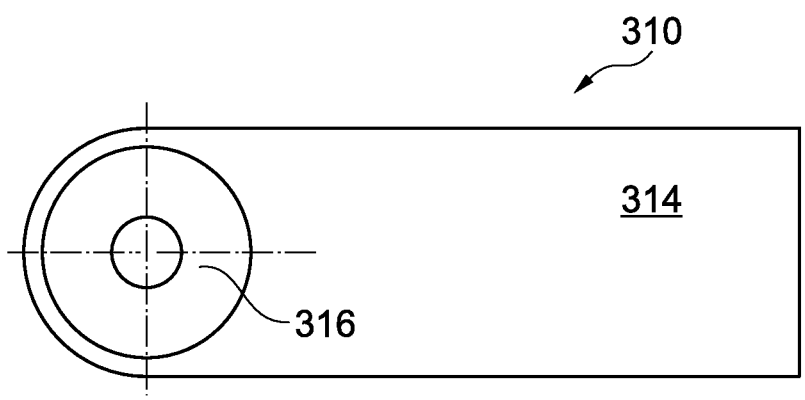
FIG. 36 is a bottom view of one embodiment of a dressing product.
Figure 37:
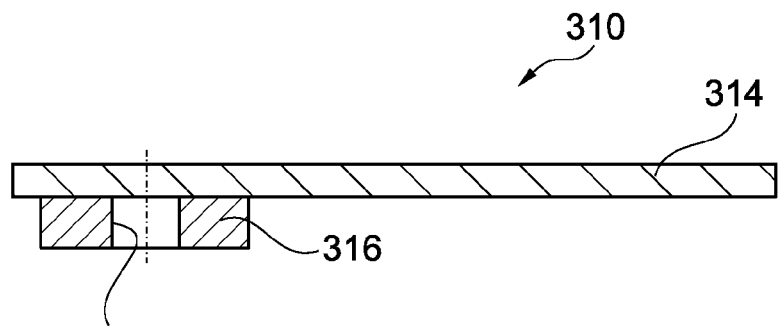

A further embodiment of a dressing product 310 is shown in FIGS. 34-37, the carrier system of which comprises a protective sheet 312 with a cut-out section 313 and a combined supporting and gripping sheet 314 (FIGS. 36 and 37). In the initial configuration of the dressing product (not shown), sheet 314 with ring-shaped member 316 adhere to the upper surface of the dressing sheet 102. Once the protective sheet 312 has been peeled off the adhesive 106, the supporting sheet 314 is used for applying the dressing product to the application site, and once application is effected, the supporting sheet 314 is separated from the backing layer. When the dressing sheet 102 is pressed against the application site by means of sheet 314, the dressing sheet 102 may deflect slightly into cavity 317, so that a gel, ointment, cream or other liquid substance applied to the adhering surface 106 is not mashed across the adhering surface 106.

Figure 38:
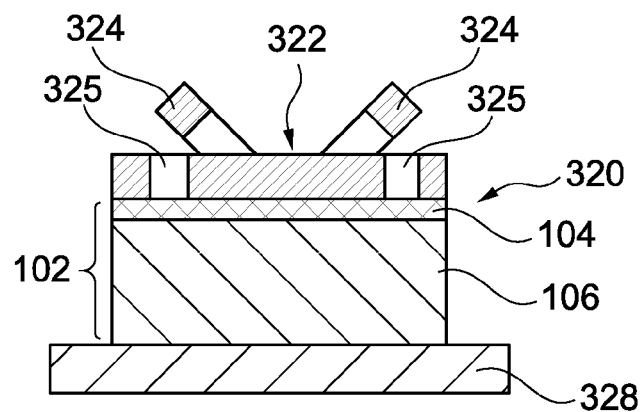
FIG. 38 is a cross-sectional view and FIG. 39 is a top view of one embodiment of a dressing product.
Figure 39:
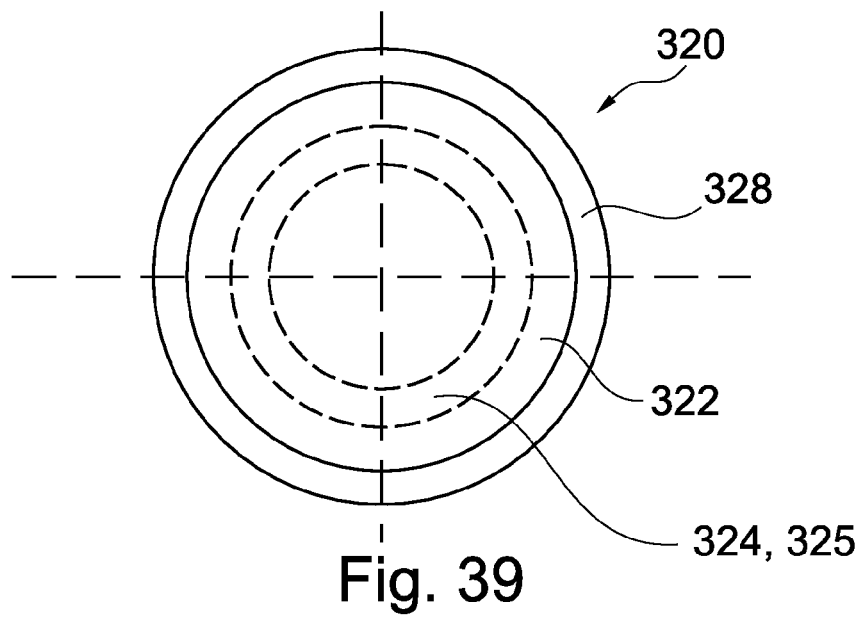

In a dressing product 320 as shown in FIGS. 38 and 39, the carrier system comprises a liner 322 attached to the backing layer 104 of the dressing sheet 102, the liner 322 defining two foldable portions 324 which are formed by punched or cut lines in the liner 332. In the initial condition of the dressing product 320, the foldable portions 324 extend in the plane of FIG. 36 and are essentially planar with the remaining portions of the liner 322, the foldable portions 324 being received in cut-out sections 325, see FIG. 39. The foldable portions may be folded out of the plane of FIG. 36, so as to thereby define handgrips for application of the dressing sheet. A protective sheet 328 adheres to the adhesive 106.

Figure 40:
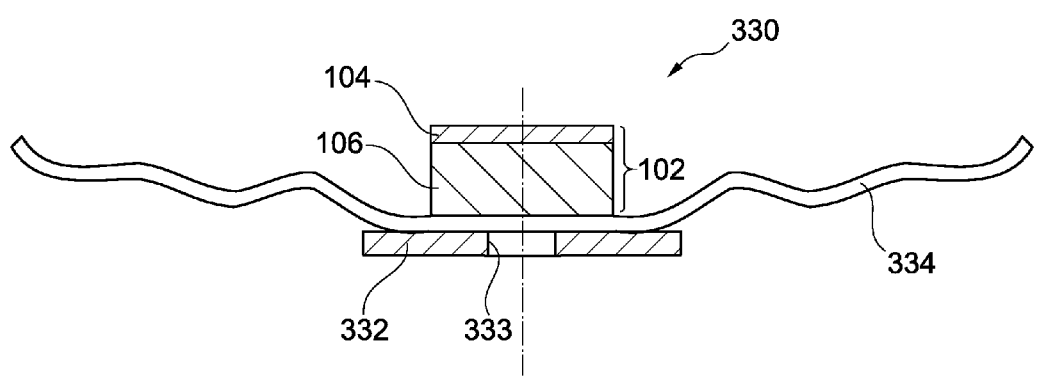
FIG. 40 is a cross-sectional view and FIG. 41 is a top view of one embodiment of a dressing product.
Figure 41:
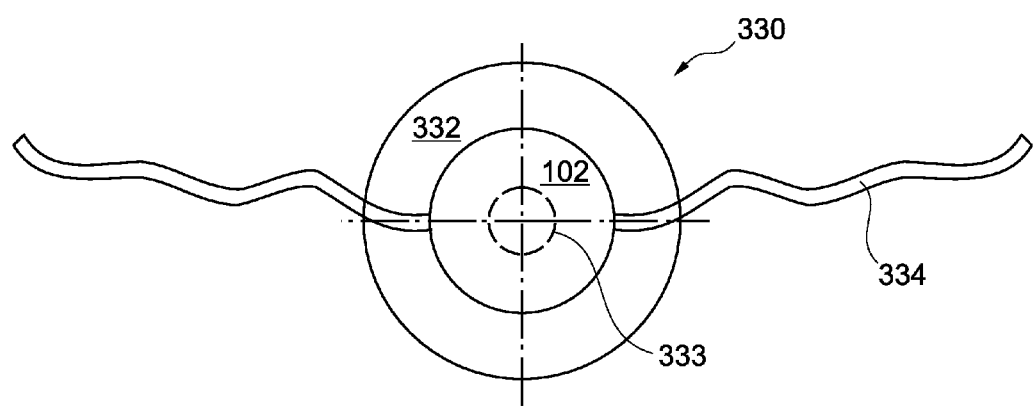

FIGS. 40 and 41 show yet a further embodiment of a dressing product 330, the carrier system of which comprises a protective sheet 332, such as a silicone coated paper sheet, with a cut-out section 333, and a thread 334. The dressing sheet 102 may be separated from the protective sheet 332 by drawing the thread away from the protective sheet 332, and subsequently the thread may be used as an applicator for the dressing sheet 102. Once the adhesive 106 of the dressing sheet 102 adheres to the application site, the thread is withdrawn by cautiously pulling it along the dressing sheet between the adhesive 106 and the application site.

Figure 42:
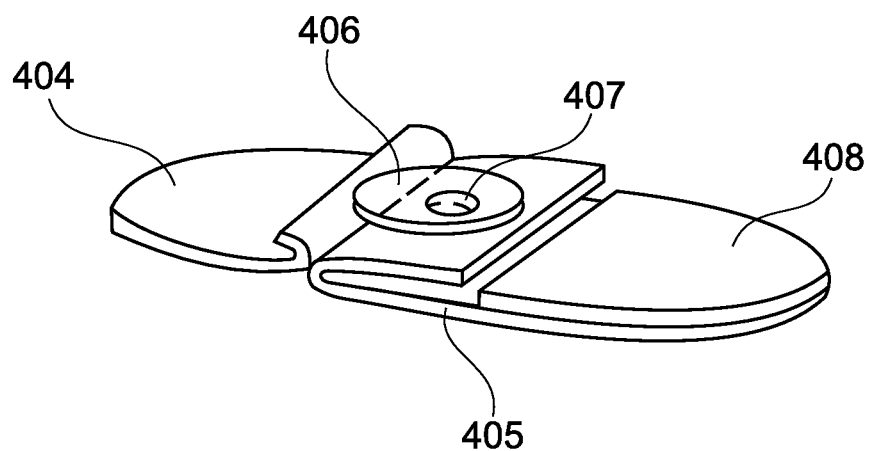
FIG. 42 is a perspective view of one embodiment of a dressing product.

FIG. 42 shows a further embodiment of the invention in perspective. The part of the protective sheet 404 extending towards the carrier systems centre is folded. The supporting sheet 405 is also provided with a fold at the central end. The supporting section 405 may further be provided with a cut-out section 407 in the folded part, e.g. for applying a pharmaceutical substance to the dressing sheet 406. The supporting section 405 may further be provided with a reinforcing layer 408, preferably in the form of a stiffer or more rigid material, such as cardboard. The dressing sheet 406 is situated on top of the folded part of the protective sheet 404 and the supporting section 405. Before application of the dressing sheet 406 to the applications site, the protective sheet 404 is pulled off, thus rolling the protective sheet 404 off the dressing sheet 406. The now partly exposed adhesive of the dressing sheet 406 is brought into contact with, and attached to, the application site and the supporting section 405 is then pulled off, thus rolling the rest of the dressing sheet 406 into contact with the application site. The presence of the two folds provides a rolling movement during application and decreases the risk of folds and wrinkles.

What is claimed is:

1. A dressing product comprising:
   a cover sheet;
   a carrier system including a periphery that is attached to the cover sheet, a lower portion that extends from the periphery to a protruding portion such that the protruding portion of the carrier system is spaced apart from the cover sheet by the lower portion of the carrier system to define a cavity between the cover sheet and the carrier system; and
   a dressing sheet including a backing layer and an adhesive attached to the backing layer, the dressing sheet disposed in the cavity and contained between sidewalls that are defined by the lower portion of the carrier system;
   wherein the adhesive attached to the backing layer faces toward and is exposed to the cavity.

2. The dressing product of claim 1, wherein the dressing sheet is removably attached to an inside surface of the protruding portion of the carrier system.

3. The dressing product of claim 1, wherein the dressing sheet is removably attached to an inside surface of the protruding portion of the carrier system with the adhesive facing toward and spaced apart from the cover sheet.

4. The dressing product of claim 1, wherein the carrier system comprises a flexible blister material configured to allow application of the dressing sheet to skin in response to finger tip pressure applied to a back surface of the carrier system when the carrier system is pressed onto an application site.

5. The dressing product of claim 1, wherein opposing ends of the dressing sheet are spaced apart from the sidewalls that are defined by the lower portion of the carrier system.

6. The dressing product of claim 1, wherein the carrier system comprises a supporting sheet having a bending stiffness that is greater than a bending stiffness of the dressing sheet.

7. The dressing product of claim 1, wherein the adhesive comprises hydrocolloid particles.

8. The dressing product of claim 1, wherein the adhesive is protected by the cover sheet.

9. The dressing product of claim 1, wherein the dressing sheet is characterized by an absence of a release liner attached to the adhesive.

* * * * *